US008198084B2

(12) United States Patent  (10) Patent No.: US 8,198,084 B2
Gorfien et al.  (45) Date of Patent: Jun. 12, 2012

(54) SERUM-FREE MAMMALIAN CELL CULTURE MEDIUM, AND USES THEREOF

(75) Inventors: Stephen F. Gorfien, Williamsville, NY (US); Richard M. Fike, Clarence, NY (US); Glenn P. Godwin, North Tonawanda, NY (US); Joyce L. Dzimian, Depew, NY (US); David A. Epstein, East Amherst, NY (US); Dale Gruber, East Amherst, NY (US); Don McClure, Indianapolis, IN (US); Paul J. Price, Grand Island, NY (US)

(73) Assignee: Life Technologies Corporation, Carlsbad, CA (US)

( * ) Notice: Subject to any disclaimer, the term of this patent is extended or adjusted under 35 U.S.C. 154(b) by 223 days.

(21) Appl. No.: 11/151,647

(22) Filed: Jun. 14, 2005

(65) Prior Publication Data

US 2006/0148074 A1 Jul. 6, 2006

Related U.S. Application Data

(63) Continuation of application No. 09/028,514, filed on Feb. 23, 1998, now abandoned, which is a continuation-in-part of application No. 08/920,875, filed on Aug. 29, 1997.

(60) Provisional application No. 60/056,829, filed on Aug. 22, 1997, provisional application No. 60/022,881, filed on Aug. 30, 1996.

(30) Foreign Application Priority Data

Sep. 2, 1997 (WO) ...................... PCT/US97/15926

(51) Int. Cl.
C12N 5/00 (2006.01)
C12N 5/02 (2006.01)
C12N 5/07 (2010.01)
C12N 5/10 (2006.01)
C12N 11/00 (2006.01)
C12N 11/16 (2006.01)

(52) U.S. Cl. ........ 435/358; 435/174; 435/383; 435/389; 435/404

(58) Field of Classification Search ........................ None
See application file for complete search history.

(56) References Cited

U.S. PATENT DOCUMENTS

| 4,673,649 | A | | 6/1987 | Boyce et al. |
| 4,767,704 | A | | 8/1988 | Cleveland et al. |
| 4,786,599 | A | | 11/1988 | Chessebeuf et al. |
| 4,853,330 | A | * | 8/1989 | Goeddel et al. ............... 435/226 |
| 4,927,762 | A | | 5/1990 | Darfler |
| 4,940,666 | A | | 7/1990 | Boyce et al. |
| 4,959,319 | A | | 9/1990 | Skelnik et al. |
| 5,017,491 | A | | 5/1991 | Freyssinet et al. |
| 5,024,947 | A | | 6/1991 | Inlow et al. |
| 5,045,454 | A | | 9/1991 | Bertheussen |
| 5,045,467 | A | | 9/1991 | Bertheussen |
| 5,063,157 | A | | 11/1991 | Stockinger |
| 5,089,397 | A | * | 2/1992 | Kushner et al. ............... 435/69.1 |
| 5,122,469 | A | | 6/1992 | Mather et al. |
| 5,135,866 | A | | 8/1992 | Heifetz et al. |
| 5,166,066 | A | | 11/1992 | Carter |
| 5,219,752 | A | | 6/1993 | Takazawa et al. |
| 5,232,848 | A | | 8/1993 | Wolfe et al. |
| 5,316,938 | A | | 5/1994 | Keen et al. |
| 5,318,898 | A | | 6/1994 | Israel |
| 5,323,848 | A | | 6/1994 | Naty et al. |
| 5,324,656 | A | * | 6/1994 | Ham et al. ..................... 435/384 |
| 5,342,777 | A | | 8/1994 | Cole et al. |
| 5,378,612 | A | | 1/1995 | Nakashima et al. |
| 5,393,558 | A | | 2/1995 | Allison et al. |
| 5,405,772 | A | | 4/1995 | Ponting |
| 5,407,669 | A | | 4/1995 | Lindstrom et al. |
| 5,422,250 | A | | 6/1995 | Mignot et al. |
| 5,443,968 | A | | 8/1995 | Takazawa et al. |
| 5,474,931 | A | | 12/1995 | DiSorbo et al. |
| 5,516,654 | A | | 5/1996 | Israel |
| 5,573,937 | A | | 11/1996 | Shinmoto et al. |
| 5,576,194 | A | | 11/1996 | Chan |
| 5,599,705 | A | | 2/1997 | Cameron |
| 5,627,159 | A | | 5/1997 | Shih et al. |
| 5,631,159 | A | | 5/1997 | Marshall et al. |

(Continued)

FOREIGN PATENT DOCUMENTS

EP  0 274 445 A2  7/1988

(Continued)

OTHER PUBLICATIONS

"Serum-Free Media, Method for Culturing animal Cells, and Process for Producing Physiologically Active Substances," PCT Gazette No. Jan. 1998, p. 275 (Jan. 1998).
JRH Biosciences Catalog No. 14602, 8 pages (1993).
Battista, P.J., et al., "Serum-free media for the culture of Chinese hamster ovary cells," *Am. Biotechnol. Lab.* 12:64-68, International Scientific Communications (1994).
Bebbington, C.R., "The use of vectors based on gene amplification for the expression of cloned genes in mammalian cells," in *DNA Cloning vol. III. A Practical Approach*, Glover, D.M., ed., IRL Press, pp. 163-188 (1987).
Berg, D.T., et al., "High-Level Expression of Secreted Proteins from Cells Adapted to Serum,-Free Suspension Culture," *BioTechniques* 14:972-978, Eaton Publishing Company (1993).

(Continued)

*Primary Examiner* — Debbie K Ware

(74) *Attorney, Agent, or Firm* — Life Technologies Corporation

(57) ABSTRACT

The present invention provides a cell culture medium formulation that supports the in vitro cultivation, particularly in suspension, of mammalian cells, particularly epithelial cells and fibroblast cells, and methods for cultivating mammalian cells in suspension in vitro using these media. The media comprise a basal medium and a polyanionic or polyanionic compound, preferably a polysulfonated or polysulfated compound, and more preferably dextran sulfate. The present invention also provides chemically defined, protein-free eukaryotic cell culture media comprising an iron chelate and zinc, which is capable of supporting the growth (and particularly the high-density growth of mammalian cells) in suspension culture, increasing the level of expression of recombinant protein in cultured cells, and/or increasing virus production in cultured cells.

13 Claims, 13 Drawing Sheets

U.S. PATENT DOCUMENTS

| | | | |
|---|---|---|---|
| 5,633,162 A | 5/1997 | Keen et al. | |
| 5,641,647 A | 6/1997 | Fischer et al. | |
| 5,707,832 A | 1/1998 | Mignot et al. | |
| 5,712,163 A | 1/1998 | Parenteau et al. | |
| 5,728,580 A * | 3/1998 | Shuler et al. | 435/348 |
| 5,824,552 A * | 10/1998 | Takazawa et al. | 435/384 |
| 5,871,986 A | 2/1999 | Boyce | |
| 5,872,005 A | 2/1999 | Wang et al. | |
| 5,945,337 A * | 8/1999 | Brown | 435/389 |
| 6,100,061 A | 8/2000 | Reiter et al. | |
| 6,103,529 A * | 8/2000 | Price et al. | 435/404 |
| 6,475,725 B1 | 11/2002 | Reiter et al. | |
| 6,936,441 B2 | 8/2005 | Reiter et al. | |
| 7,094,574 B2 | 8/2006 | Reiter et al. | |
| 7,187,286 B2 | 3/2007 | Morris et al. | |
| 7,294,484 B2 | 11/2007 | Drapeau et al. | |
| 7,601,535 B1 | 10/2009 | Weng et al. | |
| 2007/0161079 A1 | 7/2007 | Reiter et al. | |
| 2009/0253178 A1 | 10/2009 | Reiter et al. | |
| 2009/0258391 A1 | 10/2009 | Reiter et al. | |

FOREIGN PATENT DOCUMENTS

| | | |
|---|---|---|
| EP | 0 441 695 A1 | 8/1991 |
| EP | 0 481 791 A2 | 4/1992 |
| EP | 0666312 | 8/1995 |
| EP | 0 435 911 B1 | 3/1996 |
| EP | 1200561 | 6/2006 |
| GB | 901673 | 7/1962 |
| JP | 60-500748 | 5/1985 |
| JP | 63-279786 | 11/1988 |
| JP | 02-005859 | 1/1990 |
| JP | 2-49579 A | 2/1990 |
| JP | 03-500602 | 2/1991 |
| JP | 03-180176 | 8/1991 |
| JP | 04-501660 | 3/1992 |
| JP | 06-048901 | 2/1994 |
| JP | 06-500918 | 2/1994 |
| JP | 06-070757 | 3/1994 |
| JP | 2006-113879 | 4/1994 |
| JP | 08-502893 | 4/1996 |
| WO | WO 86/04920 A1 | 8/1986 |
| WO | WO 90/03430 A1 | 4/1990 |
| WO | WO 92/05246 A1 | 4/1992 |
| WO | WO 94/02592 A1 | 2/1994 |
| WO | WO 94/11525 A1 | 5/1994 |
| WO | WO-95/06112 | 3/1995 |
| WO | WO 96/14395 A1 | 5/1996 |
| WO | WO-96/15231 | 5/1996 |
| WO | WO 96/26266 A1 | 8/1996 |
| WO | WO 96/39487 A1 | 12/1996 |
| WO | WO 97/34999 A1 | 9/1997 |

OTHER PUBLICATIONS

Chaproniere-Rickenberg, D.M. and Webber, M.M., "Zinc Levels in Zinc-Stabilized Insulin are Inhibitory to the Growth of Cells in Vitro," *In Vitro* 19:373-375, Tissue Culture Assn. (1983).

Freshney, R.I., "Culture of Animal Cells," in *A Manual of Basic Technique*, Alan R. Liss, Inc. New York, pp. 80-81 (1987).

Garnier, A., et al., "Scale-up of the adenovirus expression system for the production of recombinant protein in human 293s cells," *Cytotechnol.* 15:145-155, Kluwer Academic Publishers (1994).

Gramer, M.J. and Goochee, C.F., "Glycosidase Activities in Chinese Hamster Ovary Cell Lysate and Cell Culture Supernatant," *Biotechnol. Prog.* 9:366-373, American Institute of Chemical Engineers (1993).

Gramer, M.J. and Goochee, C.F., "Glycosidase Activities of the 293 and NSO Cell Lines, and of an Antibody-Producing Hybridoma Cell Line," *Biotechnol. Bioeng.* 43:423-428, Wiley (1994).

Gramer, M.J., et al., "Removal of Sialic Acid from a Gylcoprotein in CHO Cell Culture Supernatant by Action of an Extracellular CHO Cell Sialidase," *Biotechnol.* 13:692-698, Butterworth-Heinemann (Jul. 1995).

Hall, C.V., et al., "Expression and Regulation of *Escherichia coli lacZ* Gene Fusions in Mammalian Cells," *J. Mol. Appl. Genet.* 2:101-109, Raven Press (1983).

Ham, R.G., "Clonal Growth of Mammalian Cells in a Chemically Defined, Synthetic Medium," *Proc. Natl. Acad. Sci. USA* 53:288-293, National Academy of Sciences (1965).

Ham, R.G., "Formulation of Basal Nutrient Media," in *Methods for Preparation of Media Supplements and Substrata for Serum-Free Animal Cell Culture*, Barnes, David, W., et al., Alan R. Liss, Inc. New York, pp. 3-21 (1984).

Hamilton, W.G. and Ham, R.G., "Clonal Growth of Chinese Hamster Cell Lines in Protein-Free Media," *In Vitro* 13:537-547, Tissue Culture Assn. (1977).

Kao, F.-T. and Puck, T.T., "Genetics of Somatic Mammalian Cells, VII. Induction and Isolation of Nutritional Mutants in Chinese Hamster Cells," *Proc. Natl. Acad. Sci. USA* 60:1275-1281, National Academy of Sciences (1968).

Kyung, Y.-S., et al., "High density culture of mammalian cells with dynamic perfusion based on on-line oxygen uptake rate measurements," *Cytotechnology* 14:183-190, Kluwer Academic Publishers (1994).

Lambert, K.J. and Birch, J.R., "Cell Growth Media," in *Animal Cell Biotechnology*, vol. 1, Spier, R.E. and Griffiths, J.B., eds., Academic Press, London, England, pp. 85-122 (1985).

Lao, M.-S., et al., "Degradative activities in a recombinant chinese hamster ovary cell culture," *Cytotechnology* 22:43-52, Kluwer Academic Publishers (Dec. 1996).

Le Gros, G.S., et al., "The Effects of Sodium Butyrate on Lymphokine Production," *Lymphokine Research* 4:221-227, Mary Ann Liebert (1985).

Maurer, H.R., "Towards Chemically-defined, Serum-free Media for Mammalian Cell Culture," in *Animal Cell Culture, a practical approach*, Freshney, R.I., ed., IRL Press, Oxford, pp. 13-31 (1986).

Peshwa, M., et al., Cultivation of Mammalian Cells as Aggregates in Bioreactors: Effect of Calcium Concentration on Spatial Distribution of Viability, *Biotechnol. Bioeng.* 41:179-187, Wiley (1993).

Subramani, S., et at, "Expression of the Mouse Dihydrofolate Reductase Complimentary Deoxyribonucleic Acid in Simian Virus 40 Vectors," *Mol. Cell. Biol.* 1:854-864, American Society for Microbiology (1981).

Wang, J.-W., et al., "Establishment of Three Adenovirus Packaging Cell Lines," *Cancer Gene Therapy* 3:S24, Nature Publishing Group (Nov. 1996).

Waymouth, C., "Osmolality of Mammalian Blood and of Media for Culture of Mammalian Cells," *In Vitro* 6:109-127, Tissue Culture Assn. (1970).

Waymouth, C., "Preparation and Use of Serum-Free Culture Media," in *Methods for Preparation of Media Supplements and Substrata for Serum-Free Animal Cell Culture*, Barnes, D.W., et ad., eds., Alan R. Liss, Inc. New York, pp. 23-68 (1984).

Waymouth, C., "Construction and Use of Synthetic Media," in *Cells and Tissues in Culture. Methods. Biology and Physiology*, vol. 1, Willmer, E.N., ed., Academic Press, pp. 99-142 (1965).

Werner, R.G. and Noé, W., "Mammalian Cell Culture, Part I: Characterization, morphology and metabolism," *Arzneim.-Forsch./Drug Res.* 43:1134-1139, Editio Cantor (1993).

Zang, M., et al., Production of Recombinant Proteins in Chinese Hamster Ovary Cells Using a Protein-Free Cell Culture Medium, *Biotechnology* 13:389-392, Butterworth-Heinemann (Apr. 1995).

Unverified English translation of WIPO Publication No. WO 96/14395 A1, cited on Form PTO/SB/08A as document FP5, 1996.

Dialog File 351, Derwent WPI, Accession No. 90-096513, English language abstract of Japanese Patent No. 2-49579 A, 1990.

Barritault, D., et al., "Is There a Ubiquitous Growth Factor in the Eye?," *Differentiation* 18:29-42, Blackwell (1981).

Boyce, S.T. and Ham, R.G., "Calcium-Regulated Differentiation of Normal Human Epidermal Keratinocytes in chemically Defined Clonal Culture and Serum-Free Serial Culture," *J. Invest. Dermatol.* 81:33S-40S, Nature Publishing Group (1983).

Cohen, S., "Isolation of a Mouse Submaxillary Gland Protein Accelerating Incisor Eruption and Eyelid Opening in the New-born Animal," *J. Biol. Chem.* 237:1555-1562, American Society for Biochemistry and Molecular Biology (1962).

Coleman, W.H. and Roberts, W.K., "Inhibitors of Animal Cell-Free Protein Synthesis From Grains," *Biochim. et Biophys. Acta* 696:239-244, Elsevier Publishing Company (1982).

Daley, J.P. and Epstein, D.A., "Growth of Human Epidermal Keratinocytes in Keratinocyte Serum-free Medium," *Focus* 12:68-71, Life Technologies Inc. (1990).

Freshney, R.I., "Culture of Animal Cells," in *A Manual of Basic Technique, 2nd ed.*, Freshney, R.I., ed., Alan R. Liss, Inc., New York, NY, pp. 80-81 (1987).

Freshney, R.I., "Culture of Animal Cells," in *A Manual of Basic Technique, 1st ed.*, Freshney, R.I., ed., Alan R. Liss, Inc., New York, NY, pp. 123-125 (1983).

Freshney, R.I., "Culture of Animal Cells," in *A Manual of Basic Technique, 1st ed.*, Freshney, R.I., ed., Alan R. Liss, Inc., New York, NY, pp. 119-128 (1983).

Freshney, R.I., "Chapter 1. Introduction," in *Culture of Epithelial Cells*, Freshney, R.I., ed., Wiley-Liss, New York, NY, pp. 1-23 (1992).

Gilchrest, B.A., et al., "Characterization and Partial Purification of Keratinocyte Growth Factor from the Hypothalamus," *J. Cell. Physiol.* 120:377-383, Wiley-Liss (1984).

Gorfien, S.F., et al., "Recombinant Protein Production by CHO Cells Cultured in a Chemically Defined Medium," presented at the meeting of the Japanese Association for Animal Cell Technology (JAACT), Yokohama, Japan (Sep. 1996).

Gorfien, S.F., et al, "Recombinant Protein Production by CHO Cells Cultured in a Chemically Defined Medium," *Animal Cell Technology: Basic and Applied Aspects* 9:247-252, Springer (Jan. 1998).

Gospodarowicz, D., "Preparations and Uses of Lipoproteins to Culture Normal Diploid and Tumor Cells Under Serum-Free Conditions," in *Methods for Preparation of Media, Supplements, and Substrata for Serum-Free Animal Cell Culture*, Barns, D.W., et al., eds., Alan R. Liss, Inc., New York, NY, pp. 69-86 (1984).

Keay, L., "Autoclavable Low Cost Serum-Free Cell Culture Media. The Growth of L Cells and BHK Cells on Peptones," *Biotechnol. Bioeng.* 17:745-764, Wiley (1975).

Konno, Y., et al., Effect of Zinc on in Vitro Cell Growth Using Serum-Free Culture Media, *Cell Struct. Funct.* 4:371, Japan Society for Cell Biology (1979).

Lasfargues, E.Y., et al., "A Serum Substitute that Can Support the Continuous Growth of Mammary Tumor Cells," *In Vitro* 8:494-500, Tissue Culture Assn. (1973).

Maciag, T., et al., "An endothelial cell growth factor from bovine hypothalamus: Identification and partial characterization," *Proc. Natl. Acad. Sci. USA* 76:5674-5678, National Academy of Sciences (1979).

Maciag, T., et al., "An Endocrine Approach to the Control of Epidermal Growth: Serum-Free Cultivation of Human Keratinocytes," *Science* 211:1452-1454, American Association for the Advancement of Science (1981).

Peehl, D.M. and Ham, R.G., "Growth and Differentiation of Human Keratinocytes Without a Feeder Layer or Conditioned Medium," *In Vitro* 16:516-525, Tissue Culture Assn. (1980).

Pirisi, L., et al., "Transformation of Human Fibroblasts and Keratinocytes with Human Papillomavirus Type 16 DNA," *J. Virol.* 61:1061-1066, American Society for Microbiology (1987).

Pittelkow, M.R. and Scott, R.E., "New Techniques for the in Vitro Culture of Human Skin Keratinocytes and Perspectives on Their Use for Grafting of Patients With Extensive Burns," *Mayo Clin. Proc.* 61:771-777, Mayo Foundation for Medical Education and Research (1986).

Schlaeger, E.-J., "The protein hydrolysate, Primatone RL, is a cost-effective multiple growth promoter of mammalian cell culture in serum-containing and serum-free media and displays anti-apoptosis properties," *J. Immunol. Meth.* 194:191-199, North-Holland Publishing Company (Aug. 1996).

Shiloach, J., et al., "Continuous Production of the Extracellular Domain of Recombinant Human $Ca^{++}$ Receptor from HEK 293 Cells using Novel Serum Free Medium," in *Animal Cell Technology*, Carrondo, M., et al., eds., Kluwer Academic Publishers, Netherlands, pp. 535-540 (Dec. 1996).

Shipley, G.D. and Pittelkow, M.R., "Control of Growth and Differentiation in Vitro of Human Keratinocytes Cultured in Serum-free Medium," *Arch. Dermatol.* 123:1541A-1544A, American Medical Assn. (1987).

Shipley, G.D., et al., "Growth of Normal Human Keratinocytes and Fibroblasts in Serum-Free Medium is Simulated by Acidic and Basic Fibroblast Growth Factor," *J. Cell. Physiol.* 138:511-518, Wiley-Liss (1989).

Letter from counsel at Eli Lilly and Company to counsel at Life Technologies, Inc. dated Nov. 30, 1998.

Stark, D.H., "The Cultivation of Human Kidney Epithelial Cells in Aggregate Culture for the Production of Recombinant Protein C," Ph.D. Thesis, Purdue University (1994).

Tilkins, M.L., et al., "Recombinant Protein Production by CHO Cells Cultured in Protein-Free and Serum-Free Media," presented at the *Cell Culture Engineering V Meeting*, San Diego, CA (Feb. 1996).

Valle, M.A., et al., "Evaluation of Porous Microcarriers in Fluidized Bed Reactor for Protein Production by HEK 293 Cells," in *New Developments and New Applications in Animal Cell Technology*, Merten, O.-W., et al., eds., Kluwer Academic Publishers, Netherlands, pp. 381-384 (Jul. 1998).

Wang, J.-W., et al., "Establishment of Three Adenovirus Packaging Cell Lines," *Conf. Suppl. Cancer Gene Ther.* 3:S24, Abstract No. P-53 (Nov. 1996).

Waymouth, C., "Preparation and Use of Serum-Free Culture Media," in *Methods for Preparation of Media, Supplements, and Substrata for Serum-Free Animal Cell Culture*, Barnes, D.W., et al., eds., Alan R. Liss, Inc., New York, NY, pp. 23-68 (1984).

Willie, Jr., J.J., et al., "Integrated Control of Growth and Differentiation of Normal Human Prokeratinocytes Cultured in Serum-Free Medium: Clonal Analyses, Growth Kinetics, and Cell Cycle Studies," *J. Cell. Physiol.* 121:31-44, Wiley-Liss (1984).

Letter from an outside researcher not employed by Life Technologies, Inc. to David Epstein and Dale Gruber.

Letter from David Epstein and Dale Gruber to an outside researcher not employed by Life Technologies, Inc.

Report of experimental results from an outside researcher not employed at Life Technologies, Inc. to David Epstein and Dale Gruber.

Bout, A et al., "Improved helper cells for RCA-free production of E1-deleted recombinant adenovirus vectors", *Conference Supplement: Cancer Gene Therapy*, vol. 3, No. 6, Abstract No. P-52, Appleton & Lange 1996, S24.

EP 04015156, European Search Report mailed Sep. 8, 2004.

EP 97941382, Supplementary Partial European Search Report mailed Dec. 17, 2002.

Keay, Leonard, "The Growth of L-Cells and Vero Cells on an Autoclavable MEM-Peptone Medium", *Biotechnology and Bioengineering*, vol. 19, John Wiley & Sons, Inc. 1977, 399-411.

PCT/US97/15296, International Search Report mailed Feb. 10, 1998.

Richmond, et al., *Biosafety in Microbiological and Biomedical Laboratories*, Government Printing Office, 3rd Edition, see: http://www.cdc.gov/OD/OHS/biosfty/bmbl/bmbl3toc.htm 1993.

Ringer, Sydney, "Concerning the Influence Exerted by Each of the Constituents of the Blood on the Contraction of the Ventricle", *Journal of Physiology*, vol. 3, 1882, 380-393.

EP10154333.8, "Extended European Search Report," mailed Jul. 19, 2010, pp. 11.

EP10154450.0, "Partial Search Report," mailed Jul. 20, 2010, pp. 12.

EP10155048.1, Extended European Search Report mailed on Sep. 24, 2010, pp. 9.

Bliem, R. et al., "Antibody production in packed bed reactors using serum-free and protein-free medium", *Cytotechnology*, 4(3) Mar. 1, 1990, 279-283.

Chun, B. H. et al., "Production of live attenuated varicella-zoster virus in human embryonic lung cells using microcarrier", *Biotechnology Techniques*, vol.10, No. 3 1996, 151-156.

Cuprak, L.J., et al., "Improved Basal Medium for Y-1 Mouse Adrenal Cortex Tumor Cells in Culture 1. Dependence of Growth and Steroid Response on Calcium Ion Concentration," *In Vitro*, vol. 15, No. 11 1979.

Jindrich, C. J. et al., "Protein free culture of Vera cells: a substrate for replication of human pathogenic viruses", *Cell Biology International*, 17(9) Sep. 1, 1993, 885-896.

Louis, C. W. et al., "Routine large-scale production of monoclonal antibodies in a protein-free culture medium," *Journal of Immunological Methods*, 56(2) Jan. 28, 1983, 221-234.

Merten, O. W. et al., "Evaluation of the New Serum-Free Medium (MDSS2) for the Production of Different Biologicals: Use of Various Cell Lines," *Cytotechnology*,vol. 14 Jan. 1, 1994 , 47-59.

Wyatt, D. et al., "Performance characteristics of a protein-free medium for mammalian suspension cells," *Animal Cell Technology* Jan. 1, 1995 , 349-356.

Zang, Michael et al., "Production of Recombinant Proteins in Chinese Hamster Ovary Cells Using a Protein-Free Cell Culture Medium," *Biotechnology*, vol. 13. No. 4 1995, 389-392.

Zhaolie, C. et al., "A Novel Serum-Free Medium for the Cultivation of Vero Cells on Microcarriers," *Biotechnology Techniques*,vol. 10, No. 6 Jun. 1, 1996 , 449-452.

Dee, K.U. and Shuler, M.L., "Optimization of an assay for baculovirus titer and design of regimes for the synchronous infection of insect cells," *Biotechnol. Prog.* 13:14-24, American Institute of Chemical Engineers (Jan. 1997).

Dee, K.U., et al., "Inducing Single-Cell Suspension of BTI-TN5B1-4 Insect Cells: I. The Use of Sulfated Polyanions to Prevent Cell Aggregation and Enhance Recombinant Protein Production," *Biotechnol. Bioeng.* 54:191-205, Wiley (May 1997).

Dee, K.U., et al., "Inducing Single-Cell Suspension of BTI-TN5B1-4 Insect Cells. II. The Effect of Sulfated Polyanions on Baculovirus infection," *Biotechnol. Bioeng.* 54:206-220, Wiley (May 1997).

Donaldson, M. and Shuler, M.L., "A Low-Cost Serum-Free Medium for the BTI-TN5B1-4 Insect Cell Line," presented at the *American Chemical Society Meeting*, New Orleans, LA (Mar. 1996).

Freshney, R. Ian, "Chapter 7. The Culture Environment: Substrate, Gas Phase, Medium, and Temperature," in: *Culture of Animal Cells, A Manual of Basic Technique*, $2^{nd}$ Ed., Alan R. Liss, Inc., New York, NY, pp. 57-84 (1987).

*Pharmacia Biotech Biodirectory*, pp. 23-30 (Jan. 1996).

*Pharmacia Biotech Biodirectory*, pp. 5-11 (Jan. 1997).

Shacter, E., "Serum-free media for bulk culture of hybridoma cells and the preparation of monoclonal antibodies," *Trends Biotech.* 7:248-253, Elsevier Science Publishers (1989).

Weiss, S.A., et al., "Serum-Free Media," in: *Insect Cell Culture Engineering*, Goosen, M.F.A., et al., eds., Marcel Dekker, Inc., New York, NY, pp. 179-194 (1993).

Partial European Search Report for European Application No. EP 97 94 1382, mailed Aug. 27, 2002.

Bailey, James E. et al., "Inverse Metabolic Engineering: A Strategy for Directed Genetic Engineering of Useful Phenotypes", *Biotechnology and Bioengineering* vol. 52, No. 1 Oct. 1, 1996 , 109-121.

Bauer, R. F. et al., "Propagation of mouse mammary tumor cell lines and production of mouse mammary tumor virus in a serum-free medium", *In Vitro* Aug. 1976 LNKD-PUBMED:186396, vol. 12, No. 8 XP002615261, ISSN: 0073-5655 Aug. 1976 , pp. 558-563..

Cinatl, J. et al., "Suspension Culture of Hela Cells in Protein-Free Medium: Sensitivity to Human Pathogenic Viruse", *Intervirology*, Karger, XX, vol. 37, No. 6 XP000565620, ISSN: 0300-5526 Nov. 1, 1994 , 361-366 pgs.

EP10154450.0, Extended Search Report mailed Jan. 12, 2011.

Gandor, Christine "Amplification and expression of recombinant genes in serum-independent Chinese hamster ovary cells", *FEBS Letters* 377 Nov. 2, 1995 , 290-294.

Gandor, Christine "Establishment and Characterization of Growth-Factor-Prototrophic Chinese Hamster Ovary (CHO) Cell Lines for the Production of Recombinant Proteins", *Abstract* Dissertation submitted to the Swiss Federal Institute of Technology Zurich 1993 , 3-5.

Lee, Kelvin H. et al., "Deregulated Expression of Cloned Transcription Factor E2F-1 in Chinese Hamster Ovary Cells Shifts Protein Patterns and Activates Growth in Protein-Free Medium", *Biotechnology and Bioengineering* vol. 50, No. 3 May 5, 1996 , 273-279.

Lee, Kelvin H. et al., "Two-Dimensional Electrophoresis of Proteins as a Tool in the Metabolic Engineering of Cell Cycle Regulation", *Biotechnology and Bioengineering* vol. 50, No. 3 May 5, 1996 , 336-340.

Pinter, C. et al., "Production of human immunodeficiency virus by chronically infected cells grown in protein-free medium", *Cell Biology International*, Academic Press, GB, vol. 19, No. 6, XP002323328,ISSN: 1065-6995, DOI: DOI: 10. 1006/CBIR.1995. 1095 Jan. 1, 1995 , pp. 507-515.

Renner, Wolfgang A. et al., "Recombinant Cyclin E Expression Activates Proliferation and Obviates Surface Attachment of Chinese Hamster Ovary (CHO) Cells in Protein-Free Medium", *Biotechnology and Bioengineering* vol. 47 Aug. 20, 1995 , 476-482.

Tamayose, K. et al., "A New Strategy for Large-Scale Preparation of High-Titer Recombinant Adeno-Associated Virus Vectors by Using Packaging Cell Lines and Sulfonated Cellulose Column Chromatograph", *Human Gene Therapy*, Mary Ann Liebert, NewYork ,NY, US, vol. 7, No. 4 Mar. 1, 1996 , pp. 507-513.

Yahi, Nouara et al., "Human T-lymphoblastoid Cells Selected fro Growth in Serum-Free Medium Provide New Tools for Study of HIV Replication and Cytopathogenicity", *Journal of Virological Methods* vol. 34, No. 2 Sep. 1, 1991 , 193-207.

Yahi, Nouara et al., "Production of a Highly Cytopathic HIV-1 Isolate from a Human Mucosal Epithelial Cell Line Cultured on Microcarrier Beads in Serum-Free Medium", *In Vitro Cellular and Developmental Biology Animal* vol. 31, No. 1 1995 , 62-66.

\* cited by examiner

SERUM-FREE MAMMALIAN CELL CULTURE MEDIUM, AND USES THEREOF

RELATED U.S. APPLICATION DATA

This is a continuation of U.S. application Ser. No. 09/028,514, filed on Feb. 23, 1998, now abandoned, which is a continuation-in-part of U.S. application Ser. No. 08/920,875, filed on Aug. 29, 1997, now abandoned, which is a non-provisional of provisional U.S. Application No. 60/056,829, filed on Aug. 22, 1997, and of provisional U.S. Application No. 60/022,881, filed on Aug. 30, 1996.

FIELD OF THE INVENTION

The present invention relates generally to cell culture medium formulations. Specifically, the present invention provides serum-free, low-protein or protein-free, defined cell culture medium formulations that facilitate the in vitro cultivation of mammalian cells in suspension. The culture media of the present invention are particularly suitable for suspension culture of epithelial cells, such as 293 human embryonic kidney cells, and fibroblast cells, such as Chinese hamster ovary (CHO) cells.

BACKGROUND OF THE INVENTION

Cell Culture Media

The requirements of mammalian cell culture in vitro comprise, in addition to basic nutritional substances, a complex series of growth factors (Werner, R. G. et al, *Mammalian Cell Cultures Part I: Characterization, morphology and metabolism, in: Arzneim.-Forsch./Drug Res.* 43:1134-1139 (1993)). Usually, these are added to the culture medium by supplying it with animal sera or protein-fractions from animal sources. However, these chemically non-defined mixtures exhibit variable lot to lot composition. Such mixtures also represent a potential source of contaminants, including viruses and mycoplasmas. For production on an industrial scale, the high price of the supplements and difficulties in downstream processing are additional considerations.

Cell culture media provide the nutrients necessary to maintain and grow cells in a controlled, artificial and in vitro environment. Characteristics and compositions of the cell culture media vary depending on the particular cellular requirements. Important parameters include osmolarity, pH, and nutrient formulations.

Media formulations have been used to cultivate a number of cell types including animal, plant and bacterial cells. Cells cultivated in culture media catabolize available nutrients and produce useful biological substances such as virus, monoclonal antibodies, hormones, growth factors and the like. Such products have therapeutic applications and, with the advent of recombinant DNA technology, cells can be engineered to produce large quantities of many of these products. Thus, the ability to cultivate cells in vitro is not only important for the study of cell physiology, but is also necessary for the production of useful substances which may not otherwise be obtained by cost-effective means.

Cell culture media formulations have been well documented in the literature and a number of media are commercially available. In early cell culture work, media formulations were based upon the chemical composition and physicochemical properties (e.g., osmolality, pH, etc.) of blood and were referred to as "physiological solutions" (Ringer, S., *J. Physiol.* 3:380-393 (1880); Waymouth, C., In: *Cells and Tissues in Culture*, Vol. 1, Academic Press, London, pp. 99-142 (1965); Waymouth, C., *In Vitro* 6:109-127 (1970)). However, cells in different tissues of the mammalian body are exposed to different microenvironments with respect to oxygen/carbon dioxide partial pressure and concentrations of nutrients, vitamins, and trace elements; accordingly, successful in vitro culture of different cell types will often require the use of different media formulations. Typical components of cell culture media include amino acids, organic and inorganic salts, vitamins, trace metals, sugars, lipids and nucleic acids, the types and amounts of which may vary depending upon the particular requirements of a given cell or tissue type.

Typically, cell culture media formulations are supplemented with a range of additives, including undefined components such as fetal bovine serum (FBS) (10-20% v/v) or extracts from animal embryos, organs or glands (0.5-10% v/v). While FBS is the most commonly applied supplement in animal cell culture media, other serum sources are also routinely used, including newborn calf, horse and human. Organs or glands that have been used to prepare extracts for the supplementation of culture media include submaxillary gland (Cohen, S., *J. Biol. Chem.* 237:1555-1565 (1961)), pituitary (Peehl, D. M., and Ham, R. G., *In Vitro* 16:516-525 (1980); U.S. Pat. No. 4,673,649), hypothalamus (Maciag, T., et al., *Proc. Natl. Acad. Sci. USA* 76:5674-5678 (1979); Gilchrest, B. A., et al., *J. Cell. Physiol.* 120:377-383 (1984)), ocular retina (Barretault, D., et al., *Differentiation* 18:2942 (1981)) and brain (Maciag, T., et al., *Science* 211:1452-1454 (1981)). These types of chemically undefined supplements serve several useful functions in cell culture media (Lambert, K. J. et al., In: *Animal Cell Biotechnology*, Vol. 1, Spier, R. E. et al., Eds., Academic Press New York, pp. 85-122 (1985)). For example, these supplements provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, serum or organ/gland extracts are commonly used as relatively low-cost supplements to provide an optimal culture medium for the cultivation of animal cells.

Unfortunately, the use of serum or organ/gland extracts in tissue culture applications has several drawbacks (Lambert, K. J. et al., In: *Animal Cell Biotechnology*, Vol 1, Spier, R. E. et al., Eds., Academic Press New York, pp. 85-122 (1985)). For example, the chemical compositions of these supplements and sera vary between lots, even from a single manufacturer. The supplements may also be contaminated with infectious agents (e.g., mycoplasma and viruses) which can seriously undermine the health of the cultured cells and the quality of the final product. The use of undefined components such as serum or animal extracts also prevents the true definition and elucidation of the nutritional and hormonal requirements of the cultured cells, thus eliminating the ability to study, in a controlled way, the effect of specific growth factors or nutrients on cell growth and differentiation in culture. Moreover, undefined supplements prevent the researcher from studying aberrant growth and differentiation and the disease-related changes in cultured cells. Finally and most importantly to those employing cell culture media in the industrial production of biological substances, serum and organ/gland extract supplementation of culture media can complicate and increase the costs of the purification of the desired substances from the culture media due to nonspecific co-purification of serum or extract proteins.

Defined Media

Improved levels of recombinant protein expression are obtained from cells grown in serum-free medium, relative to the level of expression seen in cells grown in medium supplemented with serum (Battista, P. J. et al., *Am. Biotech. Lab.* 12:64-68 (1994)). However, serum-free media may still contain one or more of a variety of animal-derived components, including albumin, fetuin, various hormones and other proteins. The presence of proteins or peptides makes purification of recombinant protein difficult, time-consuming, and expensive.

To overcome these drawbacks of the use of serum or organ/gland extracts, a number of so called "defined" media have been developed. These media, which often are specifically formulated to support the culture of a single cell type, contain no undefined supplements and instead incorporate defined quantities of purified growth factors, proteins, lipoproteins and other substances usually provided by the serum or extract supplement. Since the components (and concentrations thereof) in such culture media are precisely known, these media are generally referred to as "defined culture media." Often used interchangeably with "defined culture media" is the term "serum-free media" or "SFM." A number of SFM formulations are commercially available, such as those designed to support the culture of endothelial cells, keratinocytes, monocytes/macrophages, lymphocytes, hematopoietic stem cells, fibroblasts, chondrocytes or hepatocytes which are available from Life Technologies, Inc. (Rockville, Md.). The distinction between SFM and defined media, however, is that SFM are media devoid of serum and protein fractions (e.g., serum albumin), but not necessarily of other undefined components such as organ/gland extracts. Indeed, several SFM that have been reported or that are available commercially contain such undefined components, including several formulations supporting in vitro culture of keratinocytes (Boyce, S. T., and Ham, R. G., *J. Invest. Dermatol.* 81:33 (1983); Wille, J. J., et al, *J. Cell. Physiol.* 121:31 (1984); Pittelkow, M. R., and Scott, R. E., *Mayo Clin. Proc.* 61:771 (1986); Pirisi, L., et al., *J. Virol.* 61:1061 (1987); Shipley, G. D., and Pittelkow, M. R., *Arch. Dermatol.* 123: 1541 (1987); Shipley, G. D., et al., *J. Cell. Physiol.* 138:511-518 (1989); Daley, J. P., et al., *FOCUS (GIBCO/LTI)* 12:68 (1990); U.S. Pat. Nos. 4,673,649 and 4,940,666). SFM thus cannot be considered to be defined media in the true definition of the term.

Defined media generally provide several distinct advantages to the user. For example, the use of defined media facilitates the investigation of the effects of a specific growth factor or other medium component on cellular physiology, which may be masked when the cells are cultivated in serum- or extract-containing media. In addition, defined media typically contain much lower quantities of protein (indeed, defined media are often termed "low protein media") than those containing serum or extracts, rendering purification of biological substances produced by cells cultured in defined media far simpler and more cost-effective.

Some extremely simple defined media, which consist essentially of vitamins, amino acids, organic and inorganic salts and buffers have been used for cell culture. Such media (often called "basal media"), however, are usually seriously deficient in the nutritional content required by most animal cells. Accordingly, most defined media incorporate into the basal media additional components to make the media more nutritionally complex, but to maintain the serum-free and low protein content of the media. Examples of such components include serum albumin from bovine (BSA) or human (HSA); certain growth factors derived from natural (animal) or recombinant sources such as EGF or FGF; lipids such as fatty acids, sterols and phospholipids; lipid derivatives and complexes such as phosphoethanolamine, ethanolamine and lipoproteins; protein and steroid hormones such as insulin, hydrocortisone and progesterone; nucleotide precursors; and certain trace elements (reviewed by Waymouth, C., in: *Cell Culture Methods for Molecular and Cell Biology, Vol. 1: Methods for Preparation of Media, Supplements, and Substrata for Serum-Free Animal Cell Culture*, Barnes, D. W., et al., eds., New York: Alan R. Liss, Inc., pp. 23-68 (1984), and by Gospodarowicz, D., Id., at pp 69-86 (1984)).

The use of animal protein supplements in cell culture media, however, also has certain drawbacks. For example, there is a risk that the culture medium and/or products purified from it may be immunogenic, particularly if the supplements are derived from an animal different from the source of the cells to be cultured. If biological substances to be used as therapeutics are purified from such culture media, certain amounts of these immunogenic proteins or peptides may be co-purified and may induce an immunological reaction, up to and including anaphylaxis, in an animal receiving such therapeutics.

To obviate this potential problem, supplements derived from the same species as the cells to be cultured may be used. For example, culture of human cells may be facilitated using HSA as a supplement, while media for the culture of bovine cells would instead use BSA. This approach, however, runs the risks of introducing contaminants and adventitious pathogens into the culture medium (such as Creutzfeld-Jakob Disease (CJD) from HSA preparations, or Bovine Spongiform Encephalopathy ("Mad Cow Disease") virus from BSA preparations), which can obviously negatively impact the use of such media in the preparation of animal and human therapeutics. In fact, for such safety reasons, the biotechnology industry and government agencies are increasingly regulating, discouraging and even forbidding the use of cell culture media containing animal-derived proteins which may contain such pathogens.

Non-Animal Peptide Supplements

To overcome the limitations of the use of animal proteins in SFM, several attempts have been made to construct animal cell culture media that are completely free of animal proteins. For example, some culture media have incorporated extracts of yeast cells into the basal medium (see, for example, U.K. Patent Application No. GB 901673; Keay, L., *Biotechnol. Bioengin.* 17:745-764 (1975)) to provide sources of nitrogen and other essential nutrients. In another approach, hydrolysates of wheat gluten have been used, with or without addition of yeast extract, to promote in vitro growth of animal cells (Japanese Patent Application No. JP 249579). Still other media have been developed in which serum is replaced by enzymatic digests of meat, or of proteins such as .alpha.-lactalbumin or casein (e.g., peptone), which have been traditionally used in bacterial culture (Lasfargues, E. Y., et al., *In Vitro* 8(6):494-500 (1973); Keay, L., *Biotechnol. Bioeng.* 17:745-764 (1975); Keay, L., *Biotechnol. Bioeng.* 19:399-411 (1977); Schlager, E.-J., *J. Immunol. Meth.* 194:191-199 (1996)). None of these approaches, however, provided a culture medium optimal for the cultivation of a variety of animal cells. Moreover, extracts from certain plants, including wheat, barley, rye and oats have been shown to inhibit protein synthesis in cell-free systems derived from animal cells (Coleman, W. H., and Roberts, W. K., *Biochim. Biophys. Acta* 696:239-244 (1982)), suggesting that the use of peptides derived from these plants in cell culture media may actually inhibit, rather than stimulate, the growth of animal cells in vitro. More recently, animal cell culture SFM formulations comprising rice peptides have been described and shown to be useful in cultivation of a variety of normal and transformed animal cells (see co-pending, commonly owned U.S. Application No. 60/028,197, filed Oct. 10, 1996, the disclosure of which is incorporated herein by reference in its entirety).

Epithelial Cells

Overview

The epithelium lines the internal and external surfaces of the organs and glands of higher organisms. Because of this localization at the external interface between the environment and the organism (e.g., the skin) or at the internal interface between an organ and the interstitial space (e.g., the intestinal mucosal lining), the epithelium has a major role in the maintenance of homeostasis. The epithelium carries out this function, for example, by regulating transport and permeability of nutrients and wastes (Freshney, R. I., in: *Culture of Epithelial Cells*, Freshney, R. I., ed., New York: Wiley-Liss, pp. 1-23 (1992)).

The cells making up the epithelium are generically termed epithelial cells. These cells may be present in multiple layers as in the skin, or in a single layer as in the lung alveoli. As might be expected, the structure, function and physiology of epithelial cells are often tissue-specific. For example, the epidermal epithelial cells of the skin are organized as stratified squamous epithelium and are primarily involved in forming a protective barrier for the organism, while the secretory epithelial cells of many glands are often found in single layers of cuboidal cells that have a major role in producing secretory proteins and glycoproteins. Regardless of their location or function, however, epithelial cells are usually regenerative. That is, under normal conditions, or in response to injury or other activating stimulus, epithelial cells are capable of dividing or growing. This regenerative capacity has facilitated the in vitro manipulation of epithelial cells, to the point where a variety of primary epithelial cells and cell lines have been successfully cultivated in vitro (Freshney, Id.).

293 Cells

While the isolation and use of a variety of epithelial cells and epithelial cell lines have been reported in the literature, the human embryonic kidney cell line 293 ("293 cells"), which exhibits epithelial morphology, has proven particularly useful for studies of the expression of exogenous ligand receptors, production of viruses and expression of allogeneic and xenogeneic recombinant proteins. For example, U.S. Pat. No. 5,166,066 describes the construction of a stable 293 cell line comprising functional GABA receptors that include a benzodiazepine binding site, that have proven useful in identification and screening of candidate psychoactive drugs. 293 cells have also been used to produce viruses such as natural and recombinant adenoviruses (Garnier, A., et al., *Cytotechnol.* 15:145-155 (1994); Bout, A., et al., *Cancer Gene Therapy* 3(6):S24, abs. P-52 (1996); Wang, J.-W., et al., *Cancer Gene Therapy* 3(6):S24, abs. P-53 (1996)), which may be used for vaccine production or construction of adenovirus vectors for recombinant protein expression. Finally, 293 cells have proven useful in large-scale production of a variety of recombinant human proteins (Berg, D. T., et al., *BioTechniques* 14(6):972-978 (1993); Peshwa, M. V., et al., *Biotechnol. Bioeng.* 41:179-187 (1993); Garnier, A., et al. *Cytotechnol.* 15:145-155 (1994)).

Fibroblast Cells

Overview

Cells loosely called fibroblasts have been isolated from many different tissues and are understood to be connective tissue cells. It is clearly possible to cultivate cell lines, loosely termed fibroblastic cells, from embryonic and adult tissues. Fibroblasts cells characteristically have a "spindle" appearance. Fibroblast-like cells have morphological characteristics typical of fibroblast cells. Under a light microscope the cells appear pointed and elongated ("spindle shaped") when they grow as a monolayer on the surface of a culture vessel. Cell lines can be regarded as fibroblast or fibroblast-like after confirmation with appropriate markers, such as collagen, type I ((Freshney, R. I., in: *Culture of Epithelial Cells*, Freshney, R. I., ed., New York: Wiley-Liss, pp. 1-23 (1987)).

CHO Cells

CHO cells have been classified as both epithelial and fibroblast cells derived from the Chinese hamster ovary. A cell line started from Chinese hamster ovary (CHO-K1) (Kao, F.-T. And Puck, T. T., Proc. *Natl. Acad. Sci. USA* 60:1275-1281 (1968) has been in culture for many years but its identity is still not confirmed.

U.S. Pat. No. 5,316,938 discloses a medium for growing CHO cells in suspension which is essentially free of protein, lipid, and carbohydrate isolated from an animal source. This patent teaches that zinc is an optional ingredient and that it is preferable to supplement the medium with recombinant insulin.

U.S. Pat. No. 5,122,469 discloses a protein-free medium which facilitates the expression of recombinant protein in CHO cells. This patent teaches that it is preferable to supplement the medium with both insulin and transferrin.

Zang, M. et al., *Bio/Technology* 13:389-392 (1995) discloses a protein-free medium for growing CHO cells in suspension culture for recombinant protein expression. See also U.S. Pat. Nos. 5,316,938 and 5,122,469.

U.S. Pat. No. 4,767,704 discloses a protein-free medium which facilitates the long-term growth of antibody-producing monolayer hybridoma cells.

Suspension Cells

As noted above, most primary mammalian epithelial cells, mammalian fibroblast cells, epithelial cell lines, and fibroblast cell lines are typically grown in monolayer culture. For some applications, however, it would be advantageous to cultivate such cells as suspension cultures. For example, suspension cultures grow in a three-dimensional space. Monolayer cultures in similar-sized vessels, however, can only grow two-dimensionally on the vessel surface. Thus, suspension cultures typically result in higher cell yields, and correspondingly higher yields of biologicals (e.g., viruses, recombinant polypeptides, etc.) compared to monolayer cultures. In addition, suspension cultures are often easier to feed and scale-up, via simple addition of fresh culture media (dilution subculturing) to the culture vessel rather than trypsinization and centrifugation as is often required with monolayer cultures.

Many anchorage-dependent cells, such as primary epithelial cells, primary fibroblast cells, epithelial cell lines, and fibroblast cell lines, however, are not easily adapted to suspension culture. Since they are typically dependent upon anchorage to a substrate for optimal growth, growth of these cells in suspension may require their attachment to microcarriers such as latex or collagen beads. Thus, cells grown in this fashion, while capable of higher density culture than traditional monolayer cultures, are still technically attached to a surface; subculturing of these cells therefore requires similar steps as those described above for monolayer cultures. Furthermore, when large batch or fermenter cultures are established, a large volume of microcarriers often settles to the bottom of the culture vessel, thereby requiring a more complicated agitation mechanism to keep the microcarriers (and thus, the cells) in suspension without causing shear damage to the cells (Peshwa, M. V., et al., *Biotechnol. Bioeng.* 41:179-187 (1993)).

Although many transformed cells are capable of being grown in suspension (Freshney, R. I., *Culture of Animal Cells: A Manual of Basic Technique*, New York: Alan R. Liss, Inc., pp. 123-125 (1983)), successful suspension cultures often require relatively high-protein media or supplementation of the media with serum or serum components (such as the attachment factors fibronectin and/or vitronectin), or sophisticated perfusion culture control systems (Kyung, Y.-S., et al., *Cytotechnol.* 14:183-190 (1994)), which may be disadvantageous for the reasons discussed above. In addition, many epithelial cells when grown in suspension form aggregates or "clumps" which may interfere with successful subculturing and reduce growth rate and production of biologicals by the cultures. When clumping occurs, the overall cellular surface area exposed to medium is decreased and the cells are deprived of nutrition. As a result, growth slows, diminished cell densities are obtained, and protein expression is compromised.

Thus, there remains a need for a chemically defined, protein-free medium which facilitates the growth of mammalian cells to high density and/or increases the level of expression of recombinant protein, reduces cell clumping, and which does not require supplementation with animal proteins, such as transferrin and insulin.

There also remains a need for defined culture media, that are serum-free, and low-protein or protein-free, for the suspension cultivation of mammalian cells that are normally anchorage-dependent, including epithelial cells and fibroblast cells, such as 293 cells and CHO cells. Such culture media will facilitate studies of the effects of growth factors and other stimuli on cellular physiology, will allow easier and more cost-effective production and purification of biological substances (e.g., viruses, recombinant proteins, etc.) produced by cultured mammalian cells in the biotechnology industry, and will provide more consistent results in methods employing the cultivation of mammalian cells.

SUMMARY OF THE INVENTION

The present invention provides a method of cultivating a mammalian cell in suspension in vitro, the method comprising (a) obtaining a mammalian cell to be cultivated in suspension; and (b) contacting the cell with a serum-free cell culture medium comprising at least one polyanionic or polycationic compound, wherein the medium supports the cultivation of said cell in suspension. The present invention also relates to media for suspension culture and to compositions comprising mammalian cells in such suspension culture.

The present invention also relates to a method of replacing protein (particularly animal derived protein) in mammalian cell culture media. In particular, the invention relates to replacing transferrin and/or insulin, to media containing such replacements, and to compositions comprising mammalian cells in such media.

The present invention relates in particular to a medium referred to herein as the "suspension medium" and to a medium referred to herein as the "replacement medium."

The Suspension Medium

The present invention is directed to a serum-free cell culture medium comprising one or more polyanionic or polycationic compounds, wherein the medium is capable of supporting the suspension cultivation of a mammalian epithelial of fibroblast cells in vitro. In the suspension medium, the polyanionic compound is preferably a polysulfonated or polysulfated compound, more preferably heparin, dextran sulfate, heparan sulfate, dermatan sulfate, chondroitin sulfate, pentosan polysulfate, a proteoglycan or the like, and most preferably dextran sulfate, which preferably has a molecular weight of about 5,000 daltons.

In particular, the invention is directed to such culture media that further comprise one or more ingredients selected from the group of ingredients consisting of one or more amino acids, one or more vitamins, one or more inorganic salts, one or more sugars, one or more buffering salts, one or more lipids, one or more insulins (or insulin substitutes) and one or more transferrins (or transferrin substitutes). The preferred sugar used in the media of the invention is D-glucose, while the preferred buffer salt is N-[2-hydroxyethyl]-piperazine-N'-[2-ethanesulfonic acid] (HEPES). The invention is also directed to such culture media which may optionally comprise one or more supplements selected from the group of supplements consisting of one or more cytokines, heparin, one or more animal peptides, one or more yeast peptides and one or more plant peptides (which are preferably one or more rice peptides or one or more soy peptides). The amino acid ingredient of the present media preferably comprises one or more amino acids selected from the group consisting of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. The vitamin ingredient of the present media preferably comprises one or more vitamins selected from the group consisting of biotin, choline chloride, D-Ca$^{++}$-pantothenate, folic acid, i-inositol, niacinamide, pyridoxine, riboflavin, thiamine and vitamin $B_{12}$. The inorganic salt ingredient of the present media preferably comprises one or more inorganic salts selected from the group consisting of one or more calcium salts, $Fe(NO_3)_3$, KCl, one or more magnesium salts, one or more manganese salts, NaCl, $NaHCO_3$, $Na_2HPO_4$, one or more selenium salts, one or more vanadium salts and one or more zinc salts.

The invention is also directed to a cell culture medium comprising the ingredients ethanolamine, D-glucose, N-[2-hydroxyethyl]piperazine-N'-[2-ethanesulfonic acid] (HEPES), insulin, linoleic acid, lipoic acid, phenol red, PLURONIC® F68, putrescine, sodium pyruvate, transferrin, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, biotin, choline chloride, D-Ca$^{++}$-pantothenate, folic acid, i-inositol, niacinamide, pyridoxine, riboflavin, thiamine, vitamin $B_{12}$, one or more calcium salts, $Fe(NO_3)_3$, KCl, one or more magnesium salts, one or more manganese salts, NaCl, $NaHCO_3$, $Na_2HPO_4$, one or more selenium salts, one or more vanadium salts and one or more zinc salts, wherein each ingredient is present in an amount which supports the suspension cultivation of a mammalian epithelial cell in vitro. The invention is also directed to such media which further comprise dextran sulfate, and which optionally comprise one or more supplements selected from the group consisting of one or more cytokines, heparin, one or more animal peptides, one or more yeast peptides and one or more plant peptides (most preferably one or more rice peptides or one or more soy peptides).

The invention is also directed to a mammalian cell culture medium obtained by combining a basal medium with dextran sulfate (which preferably has a molecular weight of about 5,000 daltons), wherein the medium is capable of supporting the suspension cultivation of a mammalian epithelial or fibroblast cell in vitro. In one preferred such medium, the basal medium is obtained by combining one or more ingredients selected from the group consisting of ethanolamine, D-glucose, N-[2-hydroxyethyl]-piperazine-N'-[2-ethanesulfonic acid] (HEPES), insulin, linoleic acid, lipoic acid, phenol red, PLURONIC® F68, putrescine, sodium pyruvate, transferrin, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, biotin, choline chloride, D-Ca$^{++}$-pantothenate, folic acid, i-inositol, niacinamide, pyridoxine, riboflavin, thiamine, vitamin B$_{12}$, one or more calcium salts, Fe(NO$_3$)$_3$, KCl, one or more magnesium salts, one or more manganese salts, NaCl, NaHCO$_3$, Na$_2$HPO$_4$, one or more selenium salts, one or more vanadium salts and one or more zinc salts, wherein each ingredient is added in an amount which supports the suspension cultivation of a mammalian epithelial or fibroblast cell in vitro. The invention is also directed to a medium obtained by combining the media obtained as described above and one or more supplements selected from the group consisting of one or more cytokines, heparin, one or more animal peptides, one or more yeast peptides and one or more plant peptides (preferably one or more rice peptides or one or more soy peptides).

The media provided by the present invention may be protein-free, and may be a 1× formulation or concentrated as a 10× or higher formulation. The basal medium of the present invention comprises a number of ingredients, including amino acids, vitamins, organic and inorganic salts, sugars and other components, each ingredient being present in an amount which supports the cultivation of a mammalian epithelial cell in vitro. The medium may be used to culture a variety of mammalian cells, including primary epithelial cells (e.g., keratinocytes, cervical epithelial cells, bronchial epithelial cells, tracheal epithelial cells, kidney epithelial cells and retinal epithelial cells) and established cell lines (e.g., 293 embryonic kidney cells, HeLa cervical epithelial cells and PER-C6 retinal cells, MDBK (NBL-1) cells, CRFK cells, MDCK cells, CHO cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, GH.sub.1 cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intesting, esophagus, stomoch, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C.sub.3H/IOTI/2 cells, HSDM$_1$C$_3$ cells, KLN$_2$O$_5$ cells, McCoy cells, Mouse L cells, Strain 2071 (Mouse L) cells, L-M strain (Mouse L) cells, L-MTK.sup.- (Mouse L) cells, NCTC clones 2472 and 2555, SCC-PSA1 cells, Swiss/3T3 cells, Indian muntjac cells, SIRC cells, C$_{II}$ cells, and Jensen cells, or derivatives thereof).

Cells supported by the medium of the present invention may be derived from any animal, preferably a mammal, and most preferably a human. The cells cultivated in the present media may be normal cells or abnormal cells (i.e., transformed cells, established cells, or cells derived from diseased tissue samples). The media of the invention may also be prepared in different forms, such as dry powder media ("DPM"), as liquid media or as media concentrates.

The present invention also provides methods of cultivating mammalian epithelial or fibroblast cells using the culture medium formulations disclosed herein, comprising (a) contacting the cells with the cell culture media of the invention; and (b) cultivating the cells under conditions suitable to support cultivation of the cells. Preferably, cells cultivated according to these methods (which may include any of the cells described above) are cultivated in suspension.

The invention also provides kits for use in the cultivation of a mammalian epithelial cell. Kits according to the present invention comprise one or more containers, wherein a first container contains the culture medium of the invention. Additional kits of the invention comprise one or more containers wherein a first container contains a basal culture medium as described above and a second container contains one or more polyanionic or polycationic compounds, preferably a polysulfonated or polysulfated compound, more preferably heparin, dextran sulfate, heparan sulfate, dermatan sulfate, chondroitin sulfate, pentosan polysulfate, a proteoglycan or the like, and most preferably dextran sulfate which preferably has a molecular weight of about 5,000 daltons. These kits may further comprise one or more additional containers containing one or more supplements selected from the group consisting of one or more cytokines, heparin, one or more animal peptides, one or more yeast peptides and one or more plant peptides (which are preferably one or more rice peptides or one or more soy peptides).

The invention further provides compositions comprising the culture media of the present invention, which optionally may further comprise one or more mammalian epithelial or fibroblast cells, such as those described above, particularly one or more 293 embryonic kidney cells, PER-C6 retinal cells, and CHO cells.

The present invention further relates to methods of cultivating mammalian cells (particularly those described above and most particularly 293 embryonic kidney epithelial cells, PER-C6, and CHO cells) in suspension comprising (a) obtaining a mammalian cell to be cultivated in suspension; and (b) contacting the cell with the culture media of the invention under conditions sufficient to support the cultivation of the cell in suspension.

The present invention further relates to methods of producing a virus, and to viruses produced by these methods, the methods comprising (a) obtaining a mammalian cell, preferably a mammalian cell described above and most preferably a 293 embryonic kidney epithelial cell, PER-C6, and CHO cells, to be infected with a virus; (b) contacting the cell with a virus under conditions suitable to promote the infection of the cell by the virus; and (c) cultivating the cell in the culture medium of the invention under conditions suitable to promote the production of the virus by the cell. Viruses which may be produced according to these methods include adenoviruses, adeno-associated viruses and retroviruses.

The present invention further relates to methods of producing a polypeptide, and to polypeptides produced by these methods, the methods comprising (a) obtaining a mammalian cell, preferably a mammalian cell described above and most preferably a 293 embryonic kidney epithelial cell, PER-C6, and CHO cell, that has been genetically engineered to produce a polypeptide; and (b) cultivating the mammalian cell in the culture medium of the invention under conditions favoring the expression of the desired polypeptide by the mammalian cell.

The Replacement Medium

The present invention also provides the replacement medium, a chemically defined, protein-free eukaryotic (e.g., mammalian) cell culture medium comprising a $Fe^{2+}$ and/or $Fe^{3+}$ chelate and/or a $Zn^{2+}$ salt, and optionally at least one polyanionic or polycationic compound as defined herein, which is capable of supporting the growth (in particular, the high-density growth of any of mentioned mammalian cells, and particularly those described above, and preferably, CHO cells, PER-C6 cells, and 293 cells) in suspension culture, increasing the level of expression of recombinant protein in cultured cells, and/or increasing virus production in cultured cells. Further, the present invention provides a eukaryotic cell culture medium, obtained by combining an iron chelate and zinc, which is capable of supporting the density growth (in particular, the high-density growth of any of mentioned mammalian cells, and particularly those described above, and preferably, CHO cells, PER-C6 cells, and 293 cells) in suspension culture, increasing the level of expression of recombinant protein in cultured cells, and/or increasing virus production in cultured cells. Further, the present invention provides a method of cultivating mammalian cells, and particularly CHO cells, in suspension culture such that said cells express a recombinant protein comprising the steps of contacting said cells with the eukaryotic cell culture medium, wherein the iron chelate and zinc are present in an amount which supports the growth of mammalian cells in culture, and optionally together with a polyanionic or polycationic compound in an amount effective to reduce clumping of the cells compared to when the compound is not added, and cultivating the cells under conditions suitable to support both the growth (in particular, the high-density growth of any of mentioned mammalian cells, and particularly those described above, and preferably, CHO cells, PER-C6 cells, and 293 cells) in suspension culture, increasing the level of expression of recombinant protein in cultured cells, and/or increasing virus production in cultured cells.

The media provided by the present invention may be protein-free, and may be a 1× formulation or concentrated as a 10× or higher formulation. The basal medium of the present invention comprises a number of ingredients, including amino acids, vitamins, organic and inorganic salts, sugars and other components, each ingredient being present in an amount which supports the cultivation of a mammalian epithelial cell in vitro. The medium may be used to culture a variety of mammalian cells, including primary epithelial cells (e.g., keratinocytes, cervical epithelial cells, bronchial epithelial cells, tracheal epithelial cells, kidney epithelial cells and retinal epithelial cells) and established cell lines (e.g., 293 embryonic kidney cells, HeLa cervical epithelial cells and PER-C6 retinal cells, MDBK (NBL-1) cells, CRFK cells, MDCK cells, CHO cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13,2RA cells, WISH cells, BS-C-1 cells, LLC-$_2$ cells, Clone M-3 cells, I-10 cells, RAG cells, TCMK-1 cells, Y-1 cells, LLC-PK$_1$ cells, PK(15) cells, Mi$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intesting, esophagus, stomoch, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C$_3$H/IOTI/2 cells, HSDM$_1$C$_3$ cells, KLN$_2$O$_5$ cells, McCoy cells, Mouse L cells, Strain 2071 (Mouse L) cells, L-M strain (Mouse L) cells, L-MTK$^-$ (Mouse L) cells, NCTC clones 2472 and 2555, SCC-PSA1 cells, Swiss/3T3 cells, Indian muntjac cells, SIRC cells, C$_{II}$ cells, and Jensen cells, or derivatives thereof).

Cells supported by the medium of the present invention may be derived from any animal, preferably a mammal, and most preferably a human. The cells cultivated in the present media may be normal cells or abnormal cells (i.e., transformed cells, established cells, or cells derived from diseased tissue samples). The media of the invention may also be prepared in different forms, such as dry powder media ("DPM"), as liquid media or as media concentrates.

The present invention also provides methods of cultivating mammalian epithelial or fibroblast cells using the culture medium formulations disclosed herein, comprising (a) contacting the cells with the cell culture media of the invention; and (b) cultivating the cells under conditions suitable to support cultivation of the cells. Preferably, cells cultivated according to these methods (which may include any of the cells described above) are cultivated in suspension.

The medium of the present invention is a chemically defined formulation which contains no protein or hydrolysates of either plant or animal origin. Although the invention is not bound by any particular theory, it is believed that the ability of the medium of the present invention to facilitate the growth of mammalian cells is due to the replacement of insulin by zinc and/or the replacement of transferrin with an iron chelate. Moreover, when supplemented with dextran sulfate, the medium facilitates growth (in particular, the high-density growth of any of mentioned mammalian cells, and particularly those described above, and preferably, CHO cells, PER-C6 cells, and 293 cells) in suspension culture, increases the level of expression of recombinant protein in cultured cells, and/or increases virus production in cultured cells without clumping.

The medium of the present invention can be used to grow mammalian cells (in particular, to high-density) of any of mentioned mammalian cells, and particularly those described above, and preferably, CHO cells, PER-C6 cells, and 293 cells) to high density, to facilitate the expression of recombinant protein in such cells, and/or to increase virus production in cultured cells without clumping. The medium is advantageous because it is chemically defined, it is protein free, and it does not require supplementation with transferrin, insulin, or other proteins to facilitate cell growth and/or expression of recombinant protein. In addition, the protein-free nature of the medium of the present invention greatly simplifies the purification of recombinant protein.

The invention also provides kits for use in the cultivation of a mammalian epithelial cell. Kits according to the present invention comprise one or more containers, wherein a first container contains the culture medium of the invention. Additional kits of the invention comprise one or more containers wherein a first container contains a basal culture medium as described above and a second container contains one or more polyanionic or polycationic compounds, preferably a polysulfonated or polysulfated compound, more preferably heparin, dextran sulfate, heparan sulfate, dermatan sulfate, chondroitin sulfate, pentosan polysulfate, a proteoglycan or the like, and most preferably dextran sulfate which preferably has a molecular weight of about 5,000 daltons.

Other preferred embodiments of the present invention will be apparent to one of ordinary skill in light of the following drawings and description of the invention, and of the claims.

DETAILED DESCRIPTION OF THE INVENTION

Definitions

Figure 1:
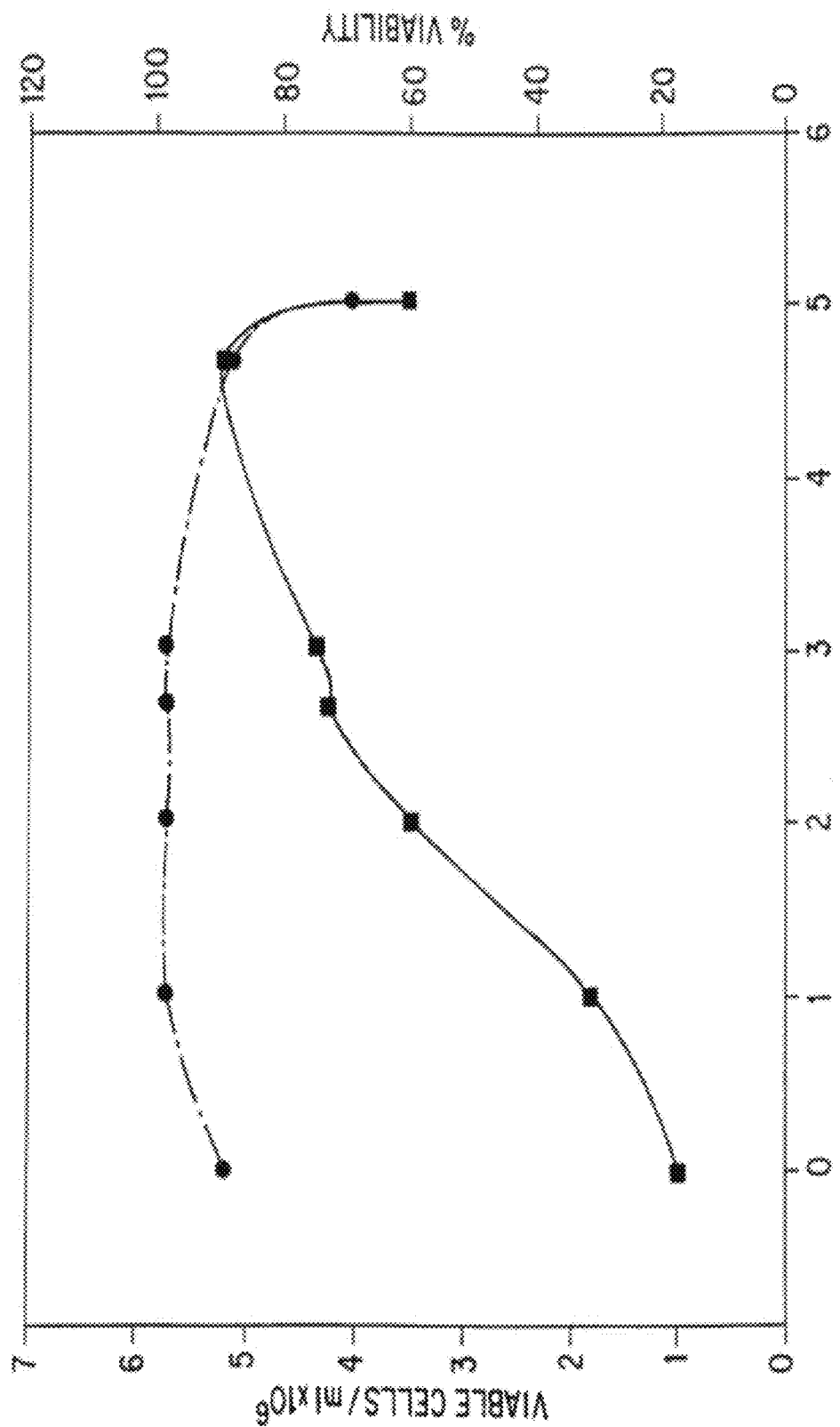
FIG. 1 depicts a line graph demonstrating cell growth (■) and percent viable cells (●), over a five-day time course, of 293 cells cultured in suspension in the suspension culture media of the invention.

In the description that follows, a number of terms conventionally used in the field of cell culture media are utilized extensively. In order to provide a clear and consistent understanding of the specification and claims, and the scope to be given such terms, the following definitions are provided.

The term "batch culture" refers to a culture allowed to progress from inoculation to conclusion without refeeding the cultured cells with fresh medium.

The term "cytokine" refers to a compound that induces a physiological response in a cell, such as growth, differentiation, senescence, apoptosis, cytotoxicity or antibody secretion. Included in this definition of "cytokine" are growth factors, interleukins, colony-stimulating factors, interferons, lymphokines and the like.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture." The media of the present invention can be used to culture any adherent mammalian cell (i.e., a cell which adheres to the culture vessel) and any mammalian cell which grows in suspension culture.

By "cultivation" is meant the maintenance of cells in vitro under conditions favoring growth, differentiation or continued viability, in an active or quiescent state, of the cells. In this sense, "cultivation" may be used interchangeably with "cell culture" or any of its synonyms described above.

By "culture vessel" is meant a glass, plastic, or metal container that can provide an aseptic environment for culturing cells.

The phrases "cell culture medium," "culture medium" (plural "media" in each case) and "medium formulation" refer to a nutritive solution for cultivating cells and may be used interchangeably.

The term "contacting" refers to the placing of cells to be cultivated in vitro into a culture vessel with the medium in which the cells are to be cultivated. The term "contacting"

encompasses mixing cells with medium, pipetting medium onto cells in a culture vessel, and submerging cells in culture medium.

The term "combining" refers to the mixing or admixing of ingredients in a cell culture medium formulation.

A "chemically defined" medium is one for which every ingredient is known. A chemically defined medium is distinguished from serum, embryonic extracts, and hydrolysates, each of which contain unknown components. The medium of the present invention is chemically defined and is free of proteins and peptides.

The term "high density" refers to a cellular density of about $1 \times 10^6$ to about $2 \times 10^7$ cells/ml. In a preferred embodiment, the term refers to a cellular density of about $1 \times 10^6$ to about $5 \times 10^6$ cells/ml in batch culture.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

Each ingredient used in cell culture media has unique physical and chemical characteristics. By "compatible ingredients" is meant those media nutrients which can be maintained in solution and form a "stable" combination.

A solution containing "compatible ingredients" is said to be "stable" when the ingredients do not degrade or decompose substantially into toxic compounds, or do not degrade or decompose substantially into compounds that can not be utilized or catabolized by the cell culture. Ingredients are also considered "stable" if degradation can not be detected or when degradation occurs at a slower rate when compared to decomposition of the same ingredient in a 1× cell culture media formulation. Glutamine, for example, in 1× media formulations, is known to degrade into pyrrolidone carboxylic acid and ammonia. Glutamine in combination with divalent cations are considered "compatible ingredients" since little or no decomposition can be detected over time. See U.S. Pat. No. 5,474,931.

Compatibility of media ingredients, in addition to stability measurements, are also determined by the "solubility" of the ingredients in solution. The term "solubility" or "soluble" refers to the ability of a ingredient to form a solution with other ingredients. Ingredients are thus compatible if they can be maintained in solution without forming a measurable or detectable precipitate. Thus, the term "compatible ingredients" as used herein refers to the combination of particular culture media ingredients which, when mixed in solution either as concentrated or 1× formulations, are "stable" and "soluble."

A "protein-free" medium is one which contains no proteins or peptides. A protein-free medium is distinguished from low-protein and essentially protein-free media, both of which contain proteins and/or peptides.

A cell culture medium is composed of a number of ingredients and these ingredients vary from one culture medium to another. A "1× formulation" is meant to refer to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic acid. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See *Methods For Preparation of Media, Supplements and Substrate For Serum-Free Animal Cell Culture*, New York: Allen R. Liss (1984), which is incorporated by reference herein in its entirety. The osmolarity and/or pH, however, may differ in a 1× formulation compared to the culture medium, particularly when fewer ingredients are contained in the 1× formulation.

A "10× formulation" is meant to refer to a solution wherein each ingredient in that solution is about 10 times more concentrated than the same ingredient in the cell culture medium. For example, a 10× formulation of RPMI-1640 culture medium may contain, among other ingredients, 2.0 g/L L-arginine, 0.5 g/L L-asparagine, and 0.2 g/L L-aspartic acid (compare 1× formulation, above). A "10× formulation" may contain a number of additional ingredients at a concentration about 10 times that found in the 1× culture medium. As will be readily apparent, "25× formulation," "50× formulation," "100× formulation," "500× formulation," and "1000×. formulation" designate solutions that contain ingredients at about 25-, 50-, 100-, 500-, or 1000-fold concentrations, respectively, as compared to a 1× cell culture medium. Again, the osmolarity and pH of the media formulation and concentrated solution may vary.

Tissues, organs and organ systems derived from animals or constructed in vitro or in vivo using methods routine in the art may similarly be cultivated in the culture media of the present invention. Animals from which cells can originate include human, monkey, ape, mouse, rat, hamster, rabbit, guinea pig, cow, swine, dog, horse, cat, goat, and sheep.

The media of the present invention can be used to grow mammalian cells in suspension culture in bioreactors, roller bottles, and microcarrier systems.

Formulation of the Suspension Culture Media

The suspension media of the present invention is generally directed to a serum-free cell culture medium comprising one or more polyanionic or polycationic compounds, wherein the medium is capable of supporting the suspension cultivation of mammalian epithelial cells (epithelial or fibroblast) in vitro. In the present media, the polyanionic compound is preferably a polysulfonated or polysulfated compound, more preferably heparin, dextran sulfate, heparan sulfate, dermatan sulfate, chondroitin sulfate, pentosan polysulfate, a proteoglycan or the like, and most preferably dextran sulfate, which preferably has a molecular weight of about 5,000 daltons. The invention also relates generally to serum-free culture media for use in suspension cultivation of a mammalian cell, comprising one or more of the above-described polyanionic or polycationic compounds, particularly dextran sulfate. In addition, the invention relates to serum-free culture media for use in producing a virus, the media comprising one or more of the above-described polyanionic or polycationic compounds, particularly dextran sulfate, wherein a virus-infected mammalian cell cultivated in suspension in the media produces a higher virus titer than a mammalian cell not cultivated in suspension in the media.

Basal and Complete Media

Any basal medium may be used in accordance with the present invention. Ingredients which the basal media of the present invention may include are amino acids, vitamin, inorganic salts, sugars, buffering salts, lipids, insulin (or insulin substitute) and transferrin (or transferrin substitute). More specifically, the basal media may contain ethanolamine, D-glucose, N-[2-hydroxyethyl]-piperazine-N'-[2-ethanesulfonic acid] (HEPES), insulin, linoleic acid, lipoic acid, phenol red, PLURONIC® F68, putrescine, sodium pyruvate. This culture medium contains no serum and therefore is considered an SFM; it is also a low-protein medium since the only protein components are insulin and transferrin. Transferrin may be in the iron-free form (i.e., apotransferrin) or in the iron-complexed form (i.e., ferrotransferrin or holotransferrin), and insulin, if present, may be human- or animal-derived and may be natural or recombinant. The medium may, of course, be made completely protein-free by not including transferrin and insulin in the formulation. Transferrin may be replaced by ferric citrate chelates at a concentration of about 10-100 µM (preferably $FeCl_3$-sodium citrate chelate at about 60 µM) or ferrous sulfate chelates at a concentration of about 10-100 µM (preferably $FeSO_4$-EDTA chelate at about 40 µM). Insulin may be replaced by one or more zinc-containing compounds such as one or more zinc salts. Zinc-containing compounds which may be used include but are not limited to $ZnCl$, $Zn(NO_3)_2$, $ZnBr$, and $ZnSO_4$, any of which may be present in their anhydrous or hydrated (i.e., ".$H_2O$") forms. Preferably, the zinc-containing compound used is $ZnSO_4.7H_2O$. In the protein-free medium of the present invention, the concentration of zinc can be optimized using only routine experimentation. Typically, the concentration of zinc in the 1× medium of the present invention may be about 0.07 to 0.73 mg/L, and is preferably about 0.354 mg/L. Each of these ingredients may be obtained commercially, for example from Sigma (Saint Louis, Mo.).

Amino acid ingredients which may be included in the media of the present invention include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. These amino acids may be obtained commercially, for example from Sigma (Saint Louis, Mo.).

Vitamin ingredients which may be included in the media of the present invention include biotin, choline chloride, D-$Ca^{++}$-pantothenate, folic acid, i-inositol, niacinamide, pyridoxine, riboflavin, thiamine and vitamin $B_{12}$. These vitamins may be obtained commercially, for example from Sigma (Saint Louis, Mo.).

Inorganic salt ingredients which may be used in the media of the present invention include one or more calcium salts (e.g., $CaCl_2$), $Fe(NO_3)_3$, KCl, one or more magnesium salts (e.g., $MgCl_2$ and/or $MgSO_4$), one or more manganese salts (e.g., $MnCl_2$), NaCl, $NaHCO_3$, $Na_2HPO_4$, and ions of the trace elements selenium, vanadium and zinc. These trace elements may be provided in a variety of forms, preferably in the form of salts such as $Na_2SeO_3$, $NH_4VO_3$ and $ZnSO_4$. These inorganic salts and trace elements may be obtained commercially, for example from Sigma (Saint Louis, Mo.).

To this basal medium, one or more polyanionic or polycationic compounds are added to formulate the complete culture media of the present invention; these compounds prevent the cells from clumping and promote growth of the cells in suspension. Thus, the complete media of the invention are capable of supporting the suspension cultivation of a mammalian cells in vitro. In the present media, the polyanionic compound is preferably a polysulfonated or polysulfated compound, more preferably heparin, dextran sulfate, heparan sulfate, dermatan sulfate, chondroitin sulfate, pentosan polysulfate, a proteoglycan or the like, which may be obtained from a number of commercial sources (such as Sigma; St. Louis, Mo.; Life Technologies, Inc.; Rockville, Md.). Particularly preferred for use in the present culture media is dextran sulfate. Dextran sulfate may be added to freshly formulated basal medium, or it may be formulated as described in detail in Example 1 in a solution of basal medium (prepared as described above). This solution of dextran sulfate may also be prepared as a 1×–1000× formulation, most preferably as a 1×, 10×, 100×, 500× or 1000× formulation, which is then diluted appropriately into culture medium to provide a 1× final formulation in the complete media of the present invention as described in detail in Example 1.

Dextran sulfate may be obtained commercially, for example from Sigma (Saint Louis, Mo.), and is preferably of an average molecular weight of about 5,000 to about 500,000 daltons, about 5,000 to about 250,000 daltons, about 5,000 to about 100,000 daltons, about 5,000 to about 50,000 daltons, about 5,000 to about 25,000 daltons, or about 5,000 to about 10,000 daltons. Most preferably the dextran sulfate used in the present culture media is of a molecular weight of about 5,000 daltons.

Polyanionic and polycationic compounds can be used in accordance with the invention for any cell, particularly epithelial cells or cell lines and fibroblast cells or cell lines, to prevent aggregation of clumping of cells cultivated in suspension. Such cells include epithelial and fibroblast cells and cell lines. Such epithelial and fibroblast cells are particularly those cells and cell lines described above, and preferably, CHO cells, PER-C6 cells, and 293 cells).

To formulate the medium of the present invention, a polyanionic or polycationic compound (and particularly, dextran sulfate) is added to the above-described basal medium in an amount effective to prevent clumping, or in an amount to effectively provide a suspension culture e.g., at a concentration of about 0-500 mg/liter, about 1-250 mg/liter, about 5-200 mg/liter, about 10-150 mg/liter or about 50-125 mg/liter, and most preferably at a concentration of about 100 mg/liter. Similar concentrations may be used for other polyanionic and polycationic compounds, such as those described above, for formulating the complete media of the invention.

The specific combinations of the above ingredients, their concentration ranges and preferred concentrations, in one example of the culture media of the invention are shown in Table 1. Although this specific example uses dextran sulfate, it is to be understood that any of the above-described polyanionic or polycationic compounds may be used in the present media.

The above ingredients listed in Table 1, when admixed together in solution, form a complete culture medium of the present invention. These complete media are suitable for use in the culture of a variety of mammalian cells, as described in more detail below. In particular, the complete media of the invention may be used to support cultivation of mammalian cells in suspension, particularly those that ordinarily are cultivated in monolayers, as described below. However, the present media are also suitable for cultivating mammalian cells under standard monolayer conditions.

TABLE 1

TYPICAL ANIMAL EPITHELIAL CELL CULTURE MEDIUM COMPONENT CONCENTRATIONS.

| Component | Component Ranges (mg/L) about: | A Preferred Embodiment (mg/L) about: | Most Preferred Embodiment (mg/L) about: |
|---|---|---|---|
| Amino Acids | | | |
| L-Alanine | 0-100 | 0 | 0.00 |
| L-Arginine | 200-600 | 360 | 355.6 |
| L-Asparagine | 5-150 | 26 | 26.40 |
| L-Aspartic Acid | 10-350 | 75 | 75.00 |
| L-Cysteine | 15-150 | 58 | 57.6 |
| L-Glutamic Acid | 5-150 | 30 | 29.40 |
| L-Glutamine | 300-1200 | 600 | 585.00 |
| Glycine | 0-100 | 0 | 0.00 |
| L-Histidine | 25-200 | 42 | 42.2 |
| L-Isoleucine | 50-400 | 190 | 190.00 |
| L-Leucine | 100-500 | 280 | 280.00 |
| L-Lysine | 100-500 | 200 | 204.0 |
| L-Methionine | 25-250 | 115 | 115.00 |
| L-Phenylalanine | 15-200 | 70 | 70.00 |
| L-Proline | 0-100 | 0 | 0.00 |
| L-Serine | 5-500 | 250 | 250.00 |
| L-Threonine | 15-400 | 60 | 60.00 |
| L-Tryptophan | 5-100 | 20 | 20.00 |
| L-Tyrosine | 15-150 | 70 | 69.2 |
| L-Valine | 50-500 | 200 | 190.00 |
| Other Components | | | |
| Ethanolamine | 0.5-5 | 3 | 3.2 |
| D-Glucose | 2500-9000 | 4500 | 4500.00 |
| HEPES | 1000-7000 | 3000 | 2980.00 |
| Insulin | 5-25 | 10 | 10.00 |
| Linoleic Acid | 0.01-5.0 | 0.1 | 0.06 |
| Lipoic Acid | 0.2-15 | 2 | 2.00 |
| Phenol Red | 0.5-30 | 1 | 1.00 |
| PLURONIC F68 | 0-750 | 300 | 300.00 |
| Putrescine | 0.01-1 | 0.1 | 0.087 |
| Sodium Pyruvate | 10-500 | 110 | 110.00 |
| Transferrin | 3-100 | 5 | 5.00 |
| Vitamins | | | |
| Biotin | 0.001-1 | 0.1 | 0.097 |
| Choline Chloride | 1-100 | 14 | 14.00 |
| D-$Ca^{++}$-Pantothenate | 0.2-10 | 1 | 1.19 |
| Folic Acid | 1-100 | 5 | 5.00 |
| i-Inositol | 2-200 | 18 | 18.00 |
| Niacinamide | 0.1-10 | 1 | 1.22 |
| Pyridoxine | 0.1-10 | 0.9 | 0.85 |
| Riboflavin | 0.02-5 | 0.2 | 0.22 |
| Thiamine | 0.1-10 | 1 | 1.00 |
| Vitamin B12 | 0.05-10 | 1 | 1.03 |
| Dextran Sulfate, MW 5000 | 50-250 | 100 | 100 |
| Inorganic Salts | | | |
| calcium salt (e.g., $CaCl_2$) | 0-100 | 10 | 11.10 |
| $Fe(NO_3)_3$* | 0.25-1.5 | 0.8 | 0.810 |
| KCl | 10-500 | 275 | 276.30 |
| $MgCl_2$ | 25-150 | 75 | 76.20 |
| $MgSO_4$ | 5-150 | 25 | 24.10 |
| manganese salt (e.g., $MnCl_2$) | 0.00001-0.0005 | 0.0001 | 0.0001 |
| NaCl | 3000-9000 | 4400 | 4410.00 |
| $NaHCO_3$ | 100-4000 | 2400 | 2400.00 |
| $Na_2HPO_4$ | 10-750 | 125 | 125.00 |
| selenium salt (e.g., $Na_2SeO_3$) | 0.0000005-0.00002 | 0.000005 | 0.0000067 |
| vanadium salt (e.g., $NH_4VO_3$) | 0.00005-0.002 | 0.0006 | 0.0006 |
| zinc salt (e.g., $ZnSO_4$)* | 0.001-0.15 | 0.1 | 0.0874 |

*Concentrations of $Fe(NO_3)_3$ and zinc salt(s) may be higher in protein-free complete media (see above).

For some applications it may be preferable to further enrich the nutritional content of the complete media to support faster growth and enhanced production of biologicals by the cultured cells, and to provide a more suitable environment for the culture of fastidious mammalian cells. To accomplish such enrichment, one or more supplements may optionally be added to the basal media or the complete media of the invention. Supplements which may advantageously be added to the present media include one or more cytokines (e.g., growth factors such as EGF, aFGF, bFGF, IGF-1, IGF-2, HB-EGF, KGF, HGF and the like), heparin (to stabilize heparin-binding growth factors such as the FGFs, HB-EGF, KGF and HGF) and one or more peptides derived from animals (e.g., HSA or BSA), yeasts (e.g., yeast extract, yeastolate or yeast extract ultrafiltrate) or plants (e.g., rice or soy peptides). Cytokines, which may be natural or recombinant, are available commercially, for example from Life Technologies, Inc. (Rockville, Md.) or R&D Systems, Inc. (Rochester, Minn.) and may be added to the basal media at concentrations recommended by the manufacturer for the particular cell type to be cultured (typically a final concentration of about 0.00001-10 mg/liter). Heparin is available commercially, for example from Sigma (St Louis, Mo.), and is preferably porcine mucosa heparin used at a final concentration in the media of about 1-500 U.S.P. units/liter. Animal, yeast and plant peptides may be obtained commercially (e.g., from Sigma for animal peptides; from Difco, Norwell, Mass., for yeast peptides; and from Quest International, Norwich, N.Y., for plant peptides), or may be derived and formulated into the present culture media as described in detail in co-pending, commonly owned U.S. Application No. 60/028,197, filed Oct. 10, 1996, the disclosure of which is incorporated herein by reference in its entirety.

The basal and complete medium ingredients and optional supplements can be dissolved in a liquid carrier or maintained in dry form. If dissolved in a liquid carrier at the preferred concentrations shown in Table 1 (i.e., a "1× formulation"), the pH of the medium should be adjusted to about 7.0-7.6, preferably about 7.1-7.5, and most preferably about 7.2-7.4. The osmolarity of the medium should also be adjusted to about 260 to about 300 mOsm, preferably about 265 to about 280 mOsm, and most preferably about 265 to about 275 mOsm. The type of liquid carrier and the method used to dissolve the ingredients into solution vary and can be determined by one of ordinary skill in the art with no more than routine experimentation. Typically, the medium ingredients can be added in any order.

Preferably, the solutions comprising individual ingredients are more concentrated than the concentration of the same ingredients in a 1× media formulation. The ingredients can be 10-fold more concentrated (10× formulation), 25-fold more concentrated (25× formulation), 50-fold more concentrated (50× concentration), or 100-fold more concentrated (100× formulation). More highly concentrated formulations can be made, provided that the ingredients remain soluble and stable. See U.S. Pat. No. 5,474,931, which is directed to methods of solubilizing culture media components at high concentrations.

If the individual medium ingredients are prepared as separate concentrated solutions, an appropriate (sufficient) amount of each concentrate is combined with a diluent to produce a 1× medium formulation. Typically, the diluent used is water but other solutions including aqueous buffers, aqueous saline solution, or other aqueous solutions may be used according to the invention.

The culture media of the present invention are typically sterilized to prevent unwanted contamination. Sterilization may be accomplished, for example, by filtration through a low protein-binding membrane filter of about 0.22 μm or 0.45 μm pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1× sterile medium formulation. Autoclaving or other elevated temperature-based methods of sterilization are not favored, since many of the components of the present culture media are heat labile and will be irreversibly degraded by temperatures such as those achieved during most heat sterilization methods.

The optimal concentration ranges for the basal medium ingredients are listed in Table 1. These ingredients can be combined to form the basal mammalian cell culture medium which is then supplemented as described above with polyanionic or polycationic compounds (e.g., dextran sulfate), and optionally with one or more supplements such as one or more cytokines, heparin, and/or one or more animal, yeast or plant peptides, to formulate the complete media of the present invention. As will be readily apparent to one of ordinary skill in the art, the concentration of a given ingredient can be increased or decreased beyond the range disclosed and the effect of the increased or decreased concentration can be determined using only routine experimentation. In a preferred embodiment, the concentrations of the ingredients of the medium of the present invention are the concentrations listed in the far right column of Table 1, supplemented with polyanionic or polycationic compounds (e.g., dextran sulfate), and optionally with one or more supplements such as one or more cytokines, heparin, and one or more animal, yeast or plant peptides, as described above.

As will be readily apparent to one of ordinary skill in the art, each of the components of the culture medium may react with one or more other components in the solution. Thus, the present invention encompasses the formulations disclosed in Table 1, supplemented as described above, as well as any reaction mixture (i.e., a culture medium or other reaction mixture) which forms after, or which is obtained by, combining these ingredients.

The optimization of the present media formulations was carried out using approaches described by Ham (Ham, R. G., *Methods for Preparation of Media, Supplements and Substrata for Serum-Free Animal Culture*, Alan R. Liss, Inc., New York, pp. 3-21 (1984)) and Waymouth (Waymouth, C., *Methods for Preparation of Media, Supplements and Substrata for Serum-Free Animal Culture*, Alan R. Liss, Inc., New York, pp. 23-68 (1984)). The optimal final concentrations for medium ingredients are typically identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth or continued health of the animal cells is measured.

Formulation of the Replacement Culture Media

In the replacement media of the invention, any basal media may be used. Such basal media may contain one or more amino acids, one or more vitamins, one or more inorganic salts, one or more buffer salts, and one or more lipids. In accordance with the invention, transferrin is replaced with iron or an iron-containing compound and/or insulin is replaced with zinc or a zinc containing compound. Preferably, iron chelate compounds are used in accordance with the invention $Fe^{2+}$ and/or $Fe^{3+}$ chelate compounds which may be used include but are not limited to compounds containing an $Fe^{2+}$ and/or $Fe^{3+}$ salt and a chelator such as ethylenediaminetetraacetic acid (EDTA), ethylene glycol-bis(β-aminoethyl ether)-N,N,N',N'-tetraacetic acid (EGTA), deferoxamine mesylate, dimercaptopropanol, diethylenetriaminepentaacetic acid (DPTA), and trans-1,2-diaminocyclohexane-N,N,N', N'-tetraacetic acid (CDTA). For example, the iron chelate compound may be a ferric citrate chelate or a ferrous sulfate chelate. Preferably, the iron chelate compound used is ferrous sulphate.7H$_2$O EDTA(FeSO$_4$.7H$_2$O.EDTA, e.g., Sigma F0518, Sigma, St. Louis, Mo.). In the medium of the present invention, the concentration of $Fe^{2+}$ and/or $Fe^{3+}$ can be optimized using only routine experimentation. Typically, the concentration of $Fe^{2+}$ and/or $Fe^{3+}$ in the 1× medium of the present invention can be about 0.00028 to 0.011 g/L. Preferably, the concentration of iron is about 0.0011 g/L.

$Zn^{2+}$-containing compounds which may be used include but are not limited to ZnCl, $Zn(NO_3)_2$, ZnBr, and $ZnSO_4.7H_2O$. Preferably, the $Zn^{2+}$ compound used is zinc sulfate.7H$_2$O ($ZnSO_4.7H_2O$). In the medium of the present invention, the concentration of $Zn^{2+}$ can be optimized using only routine experimentation. Typically, the concentration of $Zn^{2+}$ in the 1× medium of the present invention can be about 0.00007 to 0.00073 g/L. Preferably, the concentration of $Zn^{2+}$ is about 0.000354 g/L.

The term "anticlumping agent" refers to a compound which reduces the degree to which of cells in culture clump together. Preferably, the anticlumping agent is a polyanionic or polycationic compound. The polyanionic compound is preferably a polysulfonated or polysulfated compound, preferably dextran sulfate, pentosan polysulfate, heparin, heparan sulfate, dermatan sulfate, chondroitin sulfate, a proteoglycan or the like. More preferably, the anticlumping agent is dextran sulfate or pentosan polysulfate. Most preferably, the anticlumping agent is dextran sulfate, which preferably has a molecular weight of about 5,000 daltons.

Anticlumping agents may be used to decrease clumping of cells grown in suspension culture, increase the level of recombinant protein expression, and/or virus production. The present invention provides a eukaryotic cell culture medium containing polyanionic or polycationic compounds (preferably, dextran sulfate) in an amount sufficient to prevent cell clumping and/or increase the level of recombinant protein expression.

The inclusion of polyanionic or polycationic compounds (preferably, dextran sulfate) in the present media inhibits cell aggregation; thus, unlike traditional serum-free media in which suspension cells tend to aggregate or form clumps, the present media promote the cultivation of single cells in suspension. The ability to cultivate cells under these suspension culture conditions provides for rapid subculturing and high-density culture, which are advantageous for applications in which mammalian cells are used to produce a variety of products such as in the biotechnology industry, as described below. Furthermore, since the present media are serum-free and low-protein or protein-free, the media may be used for rapid production and isolation of biologicals (e.g., viruses, recombinant polypeptides, etc.), and in assays measuring the binding and/or activity of a variety of ligands such as proteins, hormones, synthetic organic or inorganic drugs, etc., on mammalian cells in vitro.

Dextran sulfate and pentosan polysulfate may be obtained commercially, for example from Sigma (St. Louis, Mo.). Dextran sulfate is preferably of an average molecular weight of about 5,000 to about 500,000 daltons, about 5,000 to about 250,000 daltons, about 5,000 to about 100,000 daltons, about 5,000 to about 50,000 daltons, about 5,000 to about 25,000 daltons, or about 5,000 to about 10,000 daltons. Most preferably the dextran sulfate used in the present culture media is of a molecular weight of about 5,000 daltons.

The pH of the 1× medium of the present invention should preferably be between about 6.9 to about 7.3. The osmolarity of the 1× medium of the present invention should preferably be between about 270 to about 350 mOsm. If desired, the osmolarity can be increased by adding a suitable salt such as NaCl. If the preferred concentrations of ingredients are used (Table 2), the osmolarity should not have to be adjusted.

Medium ingredients can be dissolved in a liquid carrier or maintained in dry form. The type of liquid carrier and the method used to dissolve the ingredients into solution vary and can be determined by one of ordinary skill in the art with no more than routine experimentation.

Preferably, the solutions comprising ingredients are more concentrated than the concentration of the same ingredients in a 1× media formulation. The ingredients can be 10 fold more concentrated (10× formulation), 25 fold more concentrated (25× formulation), 50 fold more concentrated (SOX concentration), or 100 fold more concentrated (100× formulation). More highly concentrated formulations can be made, provided that the ingredients remain soluble and stable. See U.S. Pat. No. 5,474,931.

If the media ingredients are prepared as separate concentrated solutions, an appropriate (sufficient) amount of each concentrate is combined with a diluent to produce a 1× medium formulation. Typically, the diluent used is water, but other solutions including aqueous buffers, aqueous saline solution, or other aqueous solutions may be used according to the invention.

The culture medium of the present invention is typically sterilized to prevent unwanted contamination of the cell culture media. Sterilization may be accomplished, for example, by filtration after admixing the concentrated ingredients to produce a sterile culture medium. Alternatively, concentrated subgroups of ingredients may be filter-sterilized and stored as sterile solutions. These sterile concentrates can then be mixed with a sterile diluent to produce a concentrated 1× sterile medium formulation.

The medium of the present invention facilitates the growth of mammalian cells, and particularly epithelial cells and cell lines, and fibroblast cells and cell lines, as described above, and particularly to high density, increases the level of expression of recombinant protein in cultured cells, and/or increases virus production in cultured cells. Cellular metabolic energy is expended on both cell growth and recombinant protein expression. Depending on the culture conditions and the particular cell line, either cell growth or recombinant protein expression can be facilitated at the expense of the other activity.

To shift the distribution of metabolic energy from supporting cell growth to supporting protein expression, cells can be treated with sodium butyrate (De Gros, G. S. et al., *Lymphokine Res.* 4:221-227 (1985)). About 10 μM to about 10 mM sodium butyrate can be used. Preferably, about 100 μM to 1.0 mM is used. Cells can be grown to the desired density prior to the addition of sodium butyrate. After sodium butyrate has been added, cell growth slows and recombinant protein expression increases. Although treatment with sodium butyrate decreases the rate of cell growth, this decrease in growth rate is outweighed by the increase in recombinant protein production. Moreover, because the medium of the present invention is protein-free, purification of recombinant protein can be performed more quickly, more easily and less expensively than purification can be done from cells that were grown in media containing serum or protein. See also U.S. Pat. No. 5,393,558.

Dihydrofolate reductase (DHFR) catalyzes the conversion of folate to tetrahydrofolate, which is required for purine, amino acid, and nucleoside biosynthesis. The folic acid analogue methotrexate binds and inhibits DHFR, causing cell death. DHFR deficient cells (DHFR) which have been transfected with a gene of interest and a methotrexate resistance gene can be treated with methotrexate to amplify recombinant cells (Bebbington, C. R. et al., *The Use of Vectors Based on Gene Amplification for the Expression of Cloned Genes n Mammalian Cells, In: DNA Cloning, Vol. III*, Glover, D., ed., Academic Press (1987), pp. 163-188). Surviving populations of cells exposed to sequentially increasing concentrations of methotrexate contain increased levels of DHFR that result from gene amplification.

About 50 nM to about 2 µM methotrexate can be used. Preferably, about 100 nM to about 500 nM methotrexate is used. Although treatment with methotrexate may decrease overall cell density, this decrease in cell density is outweighed by the increase in recombinant protein production. Again, because the medium of the present invention is protein-free, purification of recombinant protein can be performed more quickly, more easily and less expensively than purification can be done from cells that were grown in media containing serum or protein.

The concentration ranges within which ingredients of the 1× medium are believed to support growth (and particularly the high-density growth), increase the level of expression of recombinant protein in cultured cells, and/or increases virus production in cultured, are listed in the second column of Table 2. These ingredients can be combined to form the 1× eukaryotic cell culture medium of the present invention. As will be apparent to one of ordinary skill in the art, the concentration of a given ingredient can be increased or decreased beyond the range disclosed and the effect of the increased or decreased concentration can be determined using only routine experimentation. The concentration of each ingredient in a preferred embodiment of the medium of the present invention is listed in the third column of Table 2. The concentration of each ingredient in a particularly preferred embodiment is shown in the fourth column of Table 2.

The 1× medium of the present invention can be made using a medium concentrate technology. See U.S. Pat. No. 5,474,931. Ingredients can be stored in solution. Preferably, ingredients are grouped in concentrated solutions and stored. For example, Table 2 shows suitable groups of ingredients. Stock solutions of the grouped ingredients can be made as concentrated stocks. For example, it is possible to make 10× to 100× chemical stock solutions, which can be stored as liquids or frozen in the appropriate aliquot sizes for later use.

Stock solutions offer a number of advantages. For example, a higher final concentration of a given ingredient can be used in the 1× medium. In addition, some ingredients are more stable when stored in a concentrated stock solution. Moreover, less storage volume is required for a concentrated stock solution than is required for a 1× medium. See U.S. Pat. No. 5,474,931.

In a preferred embodiment, 27.63× concentrated stock solutions of the groups of ingredients in Table 2 are prepared as followed. To prepare a 26.63× concentrated stock solution of the Acid Soluble I group of ingredients, each of the ingredients in the Acid Soluble I group of ingredients in Table 2 is added to approximately 19.33 mL of distilled water. The ingredients in the Acid Soluble I group can be added in any order. The pH of the solution is reduced to 0.80 with 5N HCl (approximately 7.4 mL) and the solution is mixed until all of the ingredients are dissolved. The final volume of the solution is 36.192 mL.

To prepare a 27.63× concentrated stock solution of the Acid Soluble II group of ingredients, sodium phosphate is first added to approximately 39.33 mL of distilled water and the solution is mixed until the sodium phosphate is completely dissolved. The pH is adjusted to 1.00 using 5N HCl (approximately 3.5 mL). The rest of the ingredients in the Acid Soluble II group in Table 2 are added (the order of addition of the rest of these ingredients is not critical). A concentrated stock solution of the trace elements can be used. The Acid Soluble H solution is mixed until all of the ingredients are dissolved. The pH final should be 1.00. If necessary, the pH should be adjusted to 1.00. The final volume of the solution is 36.192 mL.

To prepare a 27.63× concentrated stock solution of the Salts I solution, $MgCl_2$ and ascorbic acid Mg salt phosphate are added to approximately 35.83 mL of distilled water. The solution is mixed until the ingredients are dissolved. The pH is lowered to 5.5 using 5N HCl (approximately 6.0 mL). D-Ca-pantothenate, calcium nitrate, and KCl are added and mixed. After mixing, the pH should be 5.50. If necessary, the pH should be adjusted to 5.50. The final volume of the solution is 36.192 mL.

To prepare a 27.63× concentrated stock solution of the Salts II solution, PLURONIC® F-68 is added to approximately 28.23 mL of distilled water, followed by sodium phosphate. After mixing, the pH is reduced to 7.00 using 5N HCl (approximately 0.06 mL). Glucose is added, followed by the rest of the ingredients in the Salts II group of ingredients in Table 2, except for folic acid and riboflavin (the order of addition of the rest of these ingredients, except for folic acid and riboflavin, is not critical). Preferably, a 10,000× stock solution of sodium selenite in distilled water is used. The density of β-mercaptoethanol is preferably 1.114 g/mL and the density of monothioglycerol is preferably 1.250 g/mL.

In a separate container of 2 mL of distilled water protected from light, folic acid and riboflavin are added. The pH is adjusted to 11.5 using 5N HCl (approximately 7 µL) and the solution is mixed until the folic acid and riboflavin are dissolved. This solution of folic acid and riboflavin is then added to the Salts II ingredient solution. The final volume of the Salts II solution is 36.193 mL and the final pH should be 7.00. If necessary, the pH can be adjusted to 7.00.

For the Salts II solution, the PLURONIC® F-68 can be in liquid form or in powder form. For the Acid Soluble I, Acid Soluble II, Salts I or Salts II solutions, unless otherwise noted above, components can be added to solution singly or in combination.

To prepare the 1× medium of the present invention, the following procedure is preferably used. To 840.000 mL of distilled water (pH 5.61) is added 36.192 mL of a 27.63× concentrate of the Acid Soluble I group of ingredients (pH 1.77), followed by 36.192 mL of a 27.63× concentrate of the Acid Soluble II group of ingredients (pH 1.71), followed by about 9.800 mL of 5N NaOH (pH 6.8), followed by 36.192 mL of a 26.63× concentrate of the Salts I group of ingredients (pH 6.8), followed by 36.192 mL of a 26.63× concentrate of the Salts II group of ingredients (pH 6.85), followed by 1.810 mL of ferrous sulfate chelate (pH 6.85), followed by 2.22 g of $NaHCO_3$ (pH 7.16), followed by about 0.400 mL of 5N HCl (pH 7.00), followed by 0.427 g of NaCl. The final pH of the solution should be 7.00 and the final volume should be 1000 mL. The osmolarity range of the solution should be between about 320 to 330 mOsm. 40 mL of a 200 mM glutamine solution (100×) is added to the 1× medium at the time of use.

The iron chelate compound is preferably added to the 1× medium prior to filter sterilization.

Dextran sulfate can be added to the 1× medium to a final concentration of about 1 µg/ml to about 1 mg/ml. Preferably, the final concentration of dextran sulfate is about 10 to about 25 µg/ml. Dextran sulfate can be added before filter sterilization of the 1× medium. Alternatively, presterilized dextran sulfate can be added to sterile 1× medium. If dextran sulfate is to be included in a concentrated stock solution, it can be included in the Salts II group of ingredients (see Table 2). The concentration of other anticlumping agents can be determined using only routine experimentation.

As will be apparent to one of ordinary skill in the art, the ingredients may react in solution. Thus, the present invention encompasses the formulations disclosed in Table 2 as well as any reaction mixture which forms after the ingredients in Table 2 are combined.

TABLE 2

The 1X Replacement Medium Formulation

| INGREDIENT | CONCENTRATION RANGE (G/L) | PREFERRED EMBODIMENT (G/L) ABOUT | PARTICULARLY PREFERRED EMBODIMENT (G/L) |
|---|---|---|---|
| Acid Soluble I | | | |
| L-arginine | 0.1000-0.7200 | 0.4 | 0.36192 |
| L-asparagine.$H_2O$ | 0.1000-1.8000 | 0.9 | 0.90480 |
| L-aspartic acid | 0.0100-0.3600 | 0.2 | 0.18096 |
| L-glutamic acid | 0.1000-0.6000 | 0.3 | 0.27144 |
| L-histidine | 0.0600-0.3600 | 0.2 | 0.18096 |
| hydroxy-L-proline | 0.0040-0.3600 | 0.2 | 0.18096 |
| L-isoleucine | 0.1000-0.7200 | 0.4 | 0.36192 |
| L-leucine | 0.1000-1.1000 | 0.5 | 0.54288 |
| L-lysine.HCl | 0.2000-1.1000 | 0.5 | 0.54288 |
| L-methionine | 0.0500-0.2400 | 0.1 | 0.12667 |
| L-phenylalanine | 0.0900-0.4200 | 0.2 | 0.21715 |
| L-proline | 0.0500-1.1000 | 0.5 | 0.54288 |
| L-serine | 0.1000-1.1000 | 0.5 | 0.54288 |
| L-threonine | 0.1000-0.7200 | 0.4 | 0.36192 |
| L-tryptophan | 0.0200-0.4200 | 0.2 | 0.20810 |
| L-tyrosine | 0.1000-0.3600 | 0.2 | 0.18096 |
| L-valine | 0.1000-0.7200 | 0.4 | 0.36192 |
| L-cystine.2HCl | 0.0200-0.2200 | 0.1 | 0.10496 |
| Acid Soluble II | | | |
| $Na_2HPO_4$ (anhydrous) | 0.2000-2.5000 | 0.6 | 0.63336 |
| pyridoxine.HCl | 0.0010-0.0072 | 0.004 | 0.00362 |
| thiamine.HCl | 0.0010-0.0072 | 0.004 | 0.00362 |
| glutathione | 0.0006-0.0036 | 0.002 | 0.00181 |
| zinc sulfate.$7H_2O$ | 0.0003-0.0032 | 0.002 | 0.00156 |
| cupric sulfate.$5H_2O$ | 0.000001-0.000009 | 0.000005 | 0.000004524 |
| cadmium chloride.$5H_2O$ | 0.000004-0.000040 | 0.00002 | 0.000020629 |
| cobalt chloride.$6H_2O$ | 0.0000006-0.0000086 | 0.000004 | 0.000004343 |
| stannous chloride.$2H_2O$ | 0.00000001-0.00000020 | 0.0000001 | 0.000000101 |
| manganous sulfate.$H_2O$ | 0.00000001-0.00000030 | 0.0000002 | 0.000000152 |
| nickel sulfate.$6H_2O$ | 0.00000005-00000024 | 0.0000001 | 0.000000118 |
| sodium metavanadate | 0.0000003-0000012 | 0.0000006 | 0.000000561 |
| ammonium molybdate.$4H_2O$ | 0.00000300-0.0000110 | 0.000005 | 0.000005429 |
| barium acetate | 0.00000065-0.00000240 | 0.000001 | 0.000001176 |
| potassium bromide | 0.00000003-0.00000011 | 0.00000005 | 0.000000054 |
| potassium iodide | 0.000000045-0.00000016 | 0.00000008 | 0.000000081 |
| chromium sulfate | 0.00000165-0.0000060 | 0.0000003 | 0.000000299 |
| sodium fluoride | 0.00000105-0.00000360 | 0.000002 | 0.000001810 |
| silver nitrate | 0.000000045-0.00000016 | 0.00000008 | 0.000000081 |
| rubidium chloride | 0.00000035-0.0000013 | 0.0000006 | 0.000000633 |
| zirconyl chloride | 0.0000008-0.0000029 | 0.000001 | 0.000001448 |
| aluminum chloride | 0.0000003-0.0000011 | 0.0000005 | 0.000000543 |
| germanium dioxide | 0.000000135-0.00000049 | 0.0000002 | 0.000000244 |
| titanium tetrachloride | 0.00000025-0.0000009 | 0.0000005 | 0.000000452 |
| sodium metasilicate | 0.00005-0.00095 | 0.0005 | 0.000452400 |
| Salts I | | | |
| $MgCL_2$ (anhydrous) | 0.0100-0.1400 | 0.07 | 0.06985 |
| D-Calcium pantothenate | 0.0020-0.0060 | 0.004 | 0.00362 |
| Calcium nitrate.$4H_2O$ | 0.01800-0.3600 | 0.09 | 0.09048 |
| KCl | 0.3340-1.4500 | 0.7 | 0.72384 |
| Ascorbic acid, Mg salt phosphate | 0.00199-0.040 | 0.02 | 0.01991 |
| Salts II | | | |
| Pluronic F68, 10% Solution | 5.0 mL-40.0 mL/L (0.5-4.0 g/L) | 18 mL/L (2 g/L) | 18.096 mL/L (1.8096 g/L) |
| $Na_2HPO_4$ (anhydrous) | 0.018-0.360 | 0.09 | 0.09048 |
| D-glucose | 1.000-12.60 | 6 | 6.33360 |
| folic acid | 0.002-0.0072 | 0.004 | 0.00362 |

TABLE 2-continued

The 1X Replacement Medium Formulation

| INGREDIENT | CONCENTRATION RANGE (G/L) | PREFERRED EMBODIMENT (G/L) ABOUT | PARTICULARLY PREFERRED EMBODIMENT (G/L) |
|---|---|---|---|
| riboflavin | 0.0002-0.00072 | 0.0004 | 0.000362 |
| biotin | 0.000575-0.00360 | 0.002 | 0.00181 |
| choline chloride | 0.0280-0.1810 | 0.09 | 0.09048 |
| niacinamide | 0.0003-0.00724 | 0.004 | 0.00362 |
| i-inositol | 0.0260-0.127 | 0.06 | 0.06334 |
| sodium pyruvate | 0.070-0.400 | 0.2 | 0.19906 |
| vitamin B-12 | 0.0005-0.0018 | 0.0009 | 0.00090 |
| β-mercaptoethanol | 0.00014-0.00282 | 0.001 | 0.00141 |
| para-aminobenzoic acid | 0.0010-0.00362 | 0.002 | 0.00181 |
| β-glycerophosphate | 0.090-1.800 | 0.9 | 0.90480 |
| sodium selenite | 0.00000157-0.000032 | 0.00002 | 0.0000157 |
| ethanolamine.HCl | 0.0075-0.0280 | 0.01 | 0.01357 |
| spermine | 0.0009-0.0181 | 0.009 | 0.00905 |
| putrescine.2HCl | 0.00012-0.00110 | 0.0005 | 0.000543 |
| monothioglycerol | 0.0100-0.0362 | 0.02 | 0.01810 |
| Dried powder medium | | | |
| NaHCO₃ | 1-4 | 2 | 2.22 |

The iron chelate compound is preferably added to the 1× medium prior to filter sterilization.

If glutamine is to be used, it can be added to the 1× medium prior to filter sterilization. For example, 40 ml of 200 mM L-glutamine can be added per liter of 1× medium (the final concentration of glutamine is 8 mM). If glutamine is not added, then preferably the concentrations of each of the above ingredients should be diluted 1.04-fold/L with diluent, although dilution is not necessary. Alternatively, a sterile 200 mM stock solution of L-glutamine can be added after the 1× medium has been filter sterilized.

The 1× medium does not need to be supplemented with glutamine if the glutamine synthase expression system (Celltech, Slough, UK) is used. Using this system, cells are engineered to express glutamine synthetase, which catalyzes the synthesis of glutamine from glutamate and ammonia. See U.S. Pat. No. 5,122,464.

For the 1× medium to be effective for culturing NS/O myeloma cells, a lipid mixture supplement may need to be added to the 1× medium. The lipid supplement formulation of Table 3 can be added to the 1× medium prior to filter sterilization. Preferably, a 200-400× concentrated stock solution of the lipid mixture supplement is used. In a preferred embodiment, the lipid mixture supplement is prepared as a 379× concentrated stock solution of which 2.64 ml/L is added to the 1× medium. To make the lipid supplement, ethanol is added to PLURONIC® F68 with constant stirring at 60° C. The mixture is cooled to 37-40° C. and the sterol is added. The mixture is overlaid with argon gas and is mixed until the sterol dissolves. After the sterol has dissolved, the rest of the ingredients in Table 3 are added. This lipid mixture supplement can be stored for future use. The sterol can be cholesterol or a plant sterol, such as sitosterol or stigmasterol or other plant sterol known to those of ordinary skill in the art.

TABLE 3

Lipid supplement (final concentrations in 1X Replacement medium).

| INGREDIENT | CONCENTRATION RANGE (G/L) | PREFERRED EMBODIMENT (G/L) ABOUT | PARTICULARLY PREFERRED EMBODIMENT (G/L) |
|---|---|---|---|
| Pluronic F68 | 0.1-4.0 | 1.7 | 1.74 |
| ethanol | 0.09-2.0 | 0.9 | 0.87 mL |
| cholesterol | 0.0007-0.07 | 0.007 | 0.00696 |
| lipoic acid | 0.00003-0.003 | 0.0003 | 0.000296 |
| linoleic acid | 0.00001-0.001 | 0.0001 | 0.000122 |
| α-tocopherol | 0.00002-0.002 | 0.0002 | 0.000231 |
| palmitic acid | 0.0002-0.02 | 0.002 | 0.00174 |
| oleic acid | 0.0002-0.02 | 0.002 | 0.00174 |
| dilinoleoyl phosphatidylcholine | 0.0002-0.02 | 0.002 | 0.00174 |
| stearic acid | 0.0002-0.02 | 0.002 | 0.00174 |
| linolenic acid | 0.0002-0.02 | 0.002 | 0.00174 |
| palmitoleic acid | 0.0002-0.02 | 0.002 | 0.00174 |
| myristic acid | 0.0002-0.02 | 0.002 | 0.00174 |

Kits

The invention also provides kits for use in the cultivation of a mammalian cell, and in particular a mammalian epithelial cell. Kits according to the present invention comprise one or more containers containing one or more of the media formulations of the invention. For example, a kit of the invention may comprise one or more containers wherein a first container contains a complete serum-free, low-protein or protein-free culture medium prepared as described above.

Additional kits of the invention may comprise one or more containers wherein a first container contains a basal culture medium prepared as described above and a second container contains a polyanionic or polycationic compound, preferably a polysulfonated or polysulfated compound, more preferably heparin, dextran sulfate, heparan sulfate, dermatan sulfate, chondroitin sulfate, pentosan polysulfate, a proteoglycan or the like, and most preferably dextran sulfate. The complete media, basal media and/or dextran sulfate contained in the containers of these kits may be present as IX ready-to-use formulations, or as more concentrated solutions (for example 2×, 5×, 10×, 20×, 25×, 50×, 100×, 500×, 1000× or higher).

Additional kits of the invention may further comprise one or more additional containers containing one or more supplements selected from the group consisting of one or more cytokines, heparin, one or more animal peptides, one or more yeast peptides and one or more plant peptides. Preferred cytokines, heparin, animal peptides, yeast peptides and plant peptides for inclusion in the containers of the kits of the invention are as described above. The kits of the invention may be used to produce one or more of the culture media of the invention for use in a variety of applications as described below.

Compositions

The invention further provides compositions comprising the media of the present invention. Compositions according to this aspect of the invention may consist of one or more of the present media and optionally one or more additional components, such as one or more cells, one or more tissues, one or more organs, one or more organisms, one or more viruses, one or more proteins or peptides (such as one or more enzymes), one or more hormones, one or more nucleic acids, one or more enzyme substrates, one or more cytokines, one or more extracellular matrix components (including attachment factors), one or more antibodies, one or more detectable labeling reagents (such as fluorophores, phosphors or radiolabels), and the like.

Particularly preferred compositions of the invention comprise one or more of the present culture media and one or more mammalian cells. Mammalian cells and cell lines, as described above, can be used in the compositions of the present invention. Mammalian cells particularly suitable for use in formulating the present cell culture compositions comprising the suspension medium of the present invention include epithelial cells of human origin, which may be primary cells derived from a tissue sample such as keratinocytes, cervical epithelial cells, bronchial epithelial cells, tracheal epithelial cells, kidney epithelial cells or retinal epithelial cells, or transformed cells or established cell lines (e.g., 293 human embryonic kidney cells, HeLa cervical epithelial cells or derivatives thereof (e.g., HeLaS3), PER-C6 human retinal cells and HCAT human keratinocytes), or derivatives thereof. Most preferable for use in the present compositions of the suspension medium of the present invention are 293 human embryonic kidney cells. The cells used in such preferred compositions of the invention may be normal cells, or may optionally be diseased or genetically altered. Other mammalian cells, such as CHO cells, COS cells, VERO cells, BHK cells (including BHK-21 cells) and derivatives thereof, are also suitable for use in formulating the present cell culture compositions.

Mammalian cells and cell lines, as described above, can be used in the present compositions. Most preferable for use in the present compositions of the replacement medium of the present invention are CHO cells. The cells used in such preferred compositions of the invention may be normal cells, or may optionally be diseased or genetically altered. Other mammalian cells, such as 293 cells, COS cells, VERO cells, BHK cells (including BHK-21 cells) and derivatives thereof, are also suitable for use in formulating the present cell culture compositions.

Epithelial tissues, organs and organ systems derived from animals or constructed in vitro or in vivo using methods routine in the art may similarly be used to formulate the suspension and replacement compositions of the present invention.

The compositions of the invention may be used in a variety of medical (including diagnostic and therapeutic), industrial, forensic and research applications requiring ready-to-use cultures, particularly suspension cultures, of mammalian cells in serum-free, low-protein or protein-free media. Non-limiting examples of uses of these compositions include providing stock cell cultures; short- or long-term storage of cells, tissues, organs, organisms and the like; providing vaccination reagents; etc.

Use of Culture Media

The present cell culture media may be used to facilitate cultivation of a variety of mammalian cells in suspension or in monolayer cultures. In particular, these media may be used to cultivate mammalian epithelial cells or cell lines, as described above, particularly human epithelial cells and cell lines and fibroblast cells and cell lines. The present media advantageously facilitate the suspension cultivation of cells which are typically anchorage-dependent or grown in monolayer cultures, without the use of microcarriers such as latex or collagen beads (although cells may be cultivated on such microcarriers or beads in the present media). Methods for isolation, and suspension and monolayer cultivation, of a variety of animal cells including mammalian epithelial cells are known in the art (see, e.g., Freshney, R. I., *Culture of Animal Cells: A Manual of Basic Technique*, New York: Alan R. Liss, Inc. (1983)) and are described in further detail below and in the Examples. While the present media are particularly useful for culturing mammalian cells in suspension, it is to be understood that the media may be used in any standard cell culture protocol whether the cells are grown in suspension, in monolayers, in perfusion cultures (e.g., in hollow fiber microtube perfusion systems), on semi-permeable supports (e.g., filter membranes), in complex multicellular arrays or in any other method by which mammalian cells may be cultivated in vitro.

In a preferred embodiment, the replacement medium of the present invention is used to grow CHO cells in suspension culture. In another preferred embodiment, the replacement medium of the present invention is used to grow hybridoma cells in suspension culture. In yet another preferred embodiment, the replacement medium of the present invention can be used to culture NS/O myeloma cells in suspension culture. If NS/O myeloma cells are cultured, the replacement 1× medium of the present invention can be supplemented with a lipid mixture supplement (see Table 3).

The inclusion of a polyanionic or polycationic compound, such as dextran sulfate, in the present media inhibits the aggregation of 293 cells, CHO cells, as well as the aggregation of other mammalian cells; thus, unlike traditional serum-free media in which suspension cells tend to aggregate or form clumps, the present media promote the cultivation of single cells in suspension. The ability to cultivate cells under these suspension culture conditions provides for rapid subculturing and high-density culture, which are advantageous for applications in which mammalian cells are used to produce a variety of products such as in the biotechnology industry, as described below. Furthermore, since the present media are serum-free and low-protein or protein-free, the media may be used for rapid production and isolation of biologicals (e.g., viruses, recombinant polypeptides, etc.), and in assays measuring the binding and/or activity of a variety of ligands such as proteins, hormones, synthetic organic or inorganic drugs, etc., on mammalian cells in vitro.

Cells which can be grown in the media of the present invention are those of animal origin, including but not limited to cells obtained from mammals. Mammalian cells particularly suitable for cultivation in the present media include epithelial cells and cell lines, which may be primary cells derived from a tissue sample.

The media of the present invention may be used to culture a variety of mammalian cells, including primary epithelial cells (e.g., keratinocytes, cervical epithelial cells, bronchial epithelial cells, tracheal epithelial cells, kidney epithelial cells and retinal epithelial cells) and established cell lines (e.g., 293 embryonic kidney cells, HeLa cervical epithelial cells and PER-C6 retinal cells, MDBK (NBL-1) cells, CRFK cells, MDCK cells, CHO cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, Mi$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intesting, esophagus, stomoch, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C$_3$H/IOTI/2 cells, HSDM$_1$C$_3$ cells, KLN$_2$O$_5$ cells, McCoy cells, Mouse L cells, Strain 2071 (Mouse L) cells, L-M strain (Mouse L) cells, L-MTK$^-$ (Mouse L) cells, NCTC clones 2472 and 2555, SCC-PSA1 cells, Swiss/3T3 cells, Indian muntjac cells, SIRC cells, C$_{II}$ cells, and Jensen cells, or derivatives thereof).

Cells may be normal cells, or may optionally be abnormal (e.g., diseased or genetically altered). Other mammalian cells, such as leukemic cell lines such as K562 cells, MOLT-4 cells, M1 cells and the like, and derivatives thereof, are also suitable for cultivation in the present media.

293 human embryonic kidney cells and HeLaS3 cells are particularly preferred for growth in the suspension medium of the present invention. Chinese hamster ovary (CHO) cells, NS/O cells, and hybridoma cells are particularly preferred for growth in the replacement medium of the present invention. Especially preferred are CHO cells.

Cell lines and hybridoma lines are well known to those of ordinary skill in the art. See, for example, the ATCC Catalogue of Cell Lines and Hybridomas, 7th Edition, 1992 (American Type Culture Collection, Rockville, Md., USA), and the ATCC Catalogue of Cell Lines and Hybridomas, 8th Edition, 1996 (American Type Culture Collection, Rockville, Md., USA).

Epithelial tissues, organs and organ systems derived from animals or constructed in vitro or in vivo using methods routine in the art may similarly be cultivated in the culture media of the present invention.

Isolation of Cells

Animal cells for culturing in the media of the present invention may be obtained commercially, for example from ATCC (Rockville, Md.), Quantum Biotechnologies (Montreal, Canada) or Invitrogen (San Diego, Calif.). Alternatively, cells may be isolated directly from samples of animal tissue obtained via biopsy, autopsy, donation or other surgical or medical procedure.

Tissue should be handled using standard sterile technique and a laminar flow safety cabinet. In the use and processing of all human tissue, the recommendations of the U.S. Department of Health and Human Services/Centers for Disease Control and Prevention should be followed (Biosafety in Microbiological and Biomedical Laboratories, Richmond, J. Y. et al., Eds., U.S. Government Printing Office, Washington, D.C. 3rd Edition (1993)). The tissue should be cut into small pieces (e.g., 0.5×.0.5 cm) using sterile surgical instruments. The small pieces should be washed twice with sterile saline solution supplemented with antibiotics as above, and then may be optionally treated with an enzymatic solution (e.g., collagenase or trypsin solutions, each available commercially, for example, from Life Technologies, Inc., Rockville, Md.) to promote dissociation of cells from the tissue matrix.

The mixture of dissociated cells and matrix molecules are washed twice with a suitable physiological saline or tissue culture medium (e.g., Dulbecco's Phosphate Buffered Saline without calcium and magnesium). Between washes, the cells are centrifuged (e.g., at 200× g) and then resuspended in serum-free tissue culture medium. Aliquots are counted using an electronic cell counter (such as a Coulter Counter). Alternatively, the cells can be counted manually using a hemacytometer.

Cultivation of Cells

The isolated cells and cell lines can be cultivated according to the experimental conditions determined by the investigator. The examples below demonstrate at least one functional set of culture conditions useful for cultivation of certain mammalian cells, particularly under suspension conditions. It is to be understood, however, that the optimal plating and culture conditions for a given animal cell type can be determined by one of ordinary skill in the art using only routine experimentation. For routine monolayer culture conditions, using the media of the present invention, cells can be plated onto the surface of culture vessels without attachment factors. Alternatively, the vessels can be precoated with natural, recombinant or synthetic attachment factors or peptide fragments (e.g., collagen, fibronectin, vitronectin, laminin and the like, or natural or synthetic fragments thereof), which are available commercially for example from Life Technologies, Inc. (Rockville, Md.), R&D Systems, Inc. (Rochester, Minn.), Genzyme (Cambridge, Mass.) and Sigma (St. Louis, Mo.). Isolated cells can also be seeded into or onto a natural or synthetic three-dimensional support matrix such as a preformed collagen gel or a synthetic biopolymeric material. For suspension cultivation, cells are typically suspended in the present culture media and introduced into a culture vessel that facilitates cultivation of the cells in suspension, such as a spinner flask, perfusion apparatus, or bioreactor (see Freshney, R. I., *Culture of Animal Cells: A Manual of Basic Technique*, New York: Alan R. Liss, Inc., pp. 123-125 (1983)). Ideally, agitation of the media and the suspended cells will be minimized to avoid denaturation of media components and shearing of the cells during cultivation.

The cell seeding densities for each experimental condition can be optimized for the specific culture conditions being used. For routine monolayer culture in plastic culture vessels, an initial seeding density of $1-5\times10^5$ cells/cm$^2$ is preferable, while for suspension cultivation a higher seeding density (e.g., $5-20\times10^5$ cells/cm$^2$) may be used.

Mammalian cells are typically cultivated in a cell incubator at about 37° C. The incubator atmosphere should be humidified and should contain about 3-10% carbon dioxide in air, more preferably about 8-10% carbon dioxide in air and most preferably about 8% carbon dioxide in air, although cultivation of certain cell lines may require as much as 20% carbon dioxide in air for optimal results. Culture medium pH should be in the range of about 7.1-7.6, preferably about 7.1-7.4, and most preferably about 7.1-7.3.

Cells in closed or batch culture should undergo complete medium exchange (i.e., replacing spent media with fresh media) when the cells reach a density of about $1.5-2.0 \times 10^6$ cells/ml. Cells in perfusion culture (e.g., in bioreactors or fermenters) will receive fresh media on a continuously recirculating basis.

Virus Production

In addition to cultivation of mammalian cells in suspension or in monolayer cultures, the present media may be used in methods for producing viruses from mammalian cells. Such methods according to this aspect of the invention comprise (a) obtaining a mammalian cell to be infected with a virus; (b) contacting the cell with a virus under conditions suitable to promote the infection of the cell by the virus; and (c) cultivating the cell in the culture media of the invention under conditions suitable to promote the production of virus by the cell. According to the invention, the cell may be contacted with the virus either prior to, during or following cultivation of the cell in the culture media of the invention; optimal methods for infecting a mammalian cell with a virus are well-known in the art and will be familiar to one of ordinary skill. Virus-infected mammalian cells cultivated in suspension in the media of the invention may be expected to produce higher virus titers (e.g., 2-, 3-, 5-, 10-, 20-, 25-, 50-, 100-, 250-, 500-, or 1000-fold higher titers) than those cells not cultivated in suspension in the media of the invention. These methods may be used to produce a variety of mammalian viruses and viral vectors, including but not limited to adenoviruses, adeno-associated viruses, retroviruses and the like, and are most preferably used to produce adenoviruses or adeno-associated viruses. Following cultivation of the infected cells in the present media, the used culture media comprising viruses, viral vectors, viral particles or components thereof (proteins and/or nucleic acids (DNA and/or RNA)) may be used for a variety of purposes, including vaccine production, production of viral vectors for use in cell transfection or gene therapy, infection of animals or cell cultures, study of viral proteins and/or nucleic acids and the like. Alternatively, viruses, viral vectors, viral particles or components thereof may optionally be isolated from the used culture medium according to techniques for protein and/or nucleic acid isolation that will be familiar to one of ordinary skill in the art.

Recombinant Protein Production

The present culture media may also be used in methods for the production of recombinant proteins from mammalian cells, particularly from mammalian cells grown in suspension. Cell lines commonly used for recombinant protein production (e.g., CHO cells) typically produce proteins that are abnormally glycosylated (Lao, M.-S., et al., *Cytotechnol.* 22:43-52 (1996); Graner, M. J., et al., *Biotechnol.* 13:692-698 (1993); Graner, M. J., and Goochee, C. F., *Biotechnol. Prog.* 9:366-373 (1993)). However, the relatively low β-galactosidase and sialidase activities in 293 cells at neutral pH, such as those provided by the present methods, may facilitate the production of recombinant proteins that more closely resemble their natural counterparts (Graner, M. J., and Goochee, C. F., *Biotechnol. Bioeng.* 43:423-428 (1994)). Furthermore, since the present culture media provide for rapid, high-density suspension cultivation of mammalian cells, the present methods facilitate the rapid production of recombinant proteins at higher concentrations than has been possible heretofore.

Methods of producing a polypeptide according to the invention comprise (a) obtaining a mammalian cell that has been genetically engineered to produce a polypeptide; and (b) cultivating the mammalian cell in the culture media of the present invention under conditions favoring expression of the polypeptide by the mammalian cell. Optimal methods for genetically engineering a mammalian cell to express a polypeptide of interest are well-known in the art and will therefore be familiar to one of ordinary skill. Cells may be genetically engineered prior to cultivation in the media of the invention, or they may be transfected with one or more exogenous nucleic acid molecules after being placed into culture in the media. According to the invention, genetically engineered cells may be cultivated in the present culture media either as monolayer cultures, or more preferably as suspension cultures according to the methods described above. Following cultivation of the cells, the polypeptide of interest may optionally be purified from the cells and/or the used culture medium according to techniques of protein isolation that will be familiar to one of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Materials and Methods

In each of the following examples, the following materials and methods were generally used.

Unless otherwise indicated, all media and reagents were obtained from Life Technologies, Inc. (Rockville, Md.).

Suspension Media Examples

Adenovirus type 5-transformed 293 human embryonic kidney epithelial cells were obtained from ATCC(CRL 1573), and were cultured as described in Example 4 by incubation at 37° C. in a humidified atmosphere consisting of 8% $CO_2$/92% air.

Replacement Medium Examples

A. Media

CHO-S-SFM II (Life Technologies, Inc., Gaithersburg, Md.) is a low protein (<100 μg/ml) serum-free medium designed for growth and recombinant protein expression by CHO cells in suspension culture. CHO-S-SFM-II contains both insulin and transferrin.

CHO III Prototype is an essentially protein-free formulation which contains no animal-derived proteins and is designed for growth and recombinant protein expression in suspension culture. The terms "CHO III Prototype," CHO III PFM," and "CHO III" are synonymous.

CD CHO is a particularly preferred embodiment of the replacement medium of the present invention (Table 2, the particularly preferred embodiment column), to which a $Fe^{2+}$ and/or $Fe^{3+}$ chelate has been added, and is a chemically defined formulation designed for suspension culture applications. Where applicable, glutamine is also added.

All three of the above media were formulated without hypoxanthine and thymidine for DHFR amplified RCHO cultures.

B. CHO Cells

Wild-type CHO DG44 cells were obtained from Dr. Lawrence Chasin (Columbia University) and were adapted to suspension culture in CHO-S-SFM II supplemented with hypoxanthine and thymidine. Cells were maintained in CHO-S-SFM II+HT Supplement or CHO III Prototype (Life Technologies, Inc.).

To establish a recombinant bovine growth hormone (rbGH) CHO cell line, wild-type CHO-K1 cells were transfected with two plasmids: pRSVneo, containing a neomycin resistance gene, and a bGH cassette using the protocol supplied with LipofectAMINE™ Reagent (Life Technologies). Selection was conducted in the presence of the neomycin analogue, G418, at a concentration of 1.2 mg/ml. Stock cultures of RCHO cells were maintained in either CHO-S-SFM II or CHO III Prototype supplemented with 0.6 mg/ml G418 (all products from Life Technologies, Inc.).

To establish a recombinant β-galactosidase (rβ-Gal) CHO cell line, CHO cells deficient in dihydrofolate reductase (DHFR⁻) were obtained from ATCC(CRL-9096, Rockville, Md.) and transfected with two plasmids: pSV2dhfr (ATCC 37146), containing a gene for methotrexate (MTX) resistance, and pCMVβgal, which contains the lacZ cDNA. The transfection was conducted using LipofectAMINE™ Reagent, and selection was accomplished with 1.2 μM methotrexate (Sigma Chemical Co., St Louis, Mo.). Stock cultures were maintained in CHO-S-SFM II or CHO III Prototype supplemented with 0.3 μM MTX.

C. Assays

1. Recombinant bGH Quantitation by ELISA rbGH production was quantitated using the Non-Isotopic Immunoassay System for bGH Transfection Protein™ (Life Technologies Inc., Gaithersburg, Md.) following manufacturer's instructions.

2. rβ-Gal Assay rβ-Galactosidase (rβ-gal or rβeta-Gal) was measured in cell lysates using a modification of the method described by Hall et al., *J. Mol. Appl. Gen.* 2:101-109 (1983) and Miller, *Experiments in Molecular Genetics*, Cold Spring Harbor Laboratory (1972). Briefly, a 2.0 ml sample of cell suspension was collected from each sample and subjected to two freeze-thaw cycles, centrifuged at 100× g for 4 minutes, and the supernatant was saved for rβ-Galactosidase quantitation. 100 μl of each supernatant sample was added to 1.0 ml Z buffer (0.06 M $Na_2HPO_4$, 0.04M $NaH_2PO_4$, 0.01M KCl, 0.01M $MgSO_4$-$7H_2O$, 0.05M β-mercaptoethanol, pH 7.0), followed by 200 μl of o-nitrophenyl-p-D-galactoside (ONPG, 4.0 mg/ml in $dH_{2O}$) and incubated at 37° C. for 120 minutes. The reaction was halted by addition of 500 μl stop buffer (1M $Na_2CO_3$) and absorbance at 420 nm was read against a blank of the appropriate medium. Activity was calculated using the following formulae:

1. $\frac{1000 \times A_{120}}{120 \min \times 0.1 \, ml}$ = Units rβ-galactosidase 2. Units rβ-galactosidase/# of cells=Activity/cell rβ-Gal was detected in cells using the staining method of Sanes et al., *EMBO J.* 5:3133-3142 (1986).

3. Amino Acid, Ammonia, Glucose and Lactate Measurements

Amino acid and ammonia levels in culture supernatants were measured by HPLC using the Waters AccQ-Tag method (Millipore Corp., Milford, Pa.). Glucose and Lactate concentrations were determined with the YSI Select Biochemistry Analyzer (Model 2700, YSI, Yellow Springs, Ohio).

D. CHO Cell Culture

Unless indicated otherwise below, CHO cell culture conditions were as follows for the following Examples. 25-35 mL of CHO cells were cultured in 125 mL shake flasks in humidified air containing 5-10% carbon dioxide. The shake flasks were shaken on an orbital shaking platform at 125-135 rpm. Temperature was maintained at 37° C. Cells were subcultured every three to four days to a density of $2-3 \times 10^5$ cells/mL.

Example 1

Formulation of Complete Suspension Medium

Formulation of Basal Cell Culture Medium. To formulate the basal cell culture medium, the following were blended as powders: L-arginine.HCl (430.00 mg/L; 355.6 mg/L L-arginine free base), L-asparagine (anhydrous) (26.40 mg/L), L-aspartic acid (75.00 mg/L), L-cysteine (57.6 mg/L), L-glutamic acid (29.40 mg/L), L-glutamine (585.00 mg/L), L-histidine (42.15 mg/L), L-isoleucine (190.00 mg/L), L-leucine (280.00 mg/L), L-lysine (204 mg/L), L-methionine (115.00 mg/L), L-phenylalanine (70.00 mg/L), L-serine (250.00 mg/L), L-threonine (60.00 mg/L), L-tryptophan (20.00 mg/L), L-tyrosine (69.2 mg/L), L-valine (190.00 mg/L), biotin (0.097 mg/L), D-$Ca^{++}$-pantothenate (1.19 mg/L), choline chloride (14.00 mg/L), folic acid (5.00 mg/L), i-inositol (18.00 mg/L), niacinamide (1.22 mg/L), pyridoxine.HCl (1.03 mg/L; 0.85 mg/L pyridoxine free base), riboflavin (0.22 mg/L), thiamine (0.99 mg/L), vitamin $B_{12}$ (1.03 mg/L), putrescine (0.087 mg/L), D-glucose (4500.00 mg/L), KCl (276.30 mg/L), NaCl (4410.00 mg/L), HEPES (2980.00 mg/L), linoleic acid (0.06 mg/L), D,L-lipoic acid (2.00 mg/L), phenol red (1.00 mg/L), PLURONIC® F68 (300.00 mg/L), sodium pyruvate (110.0 mg/L), $Na_2HPO_4$ (125.00 mg/L), insulin (zinc human recombinant) (10.00 mg/L), transferrin (human holo-, heat-treated) (5.00 mg/L), ethanolamine.HCl (5 mg/L; 3.2 mg/L ethanolamine), $Fe(NO_3)_3.9H_2O$ (0.810 mg/L), $MgCl_2$ (76.20 mg/L), $MgSO_4$ (24.10 mg/L), $CaCl_2$ (11.10 mg/L), $ZnSO_4.H_2O$ (0.0874 mg/L), $Na_2SeO_3$ (0.0000067 mg/L), $MnCl_2$ (0.0001 mg/L) and $NH_4VO_3$ (0.0006 mg/L).

$NaHCO_3$ (2400.00 mg/L) was added to the medium solution, and the pH of the solution was then adjusted with HCl to 7.2±0.05 and the volume adjusted to the full desired volume with $ddH_2O$. The osmolality was determined to be 265-275 mOsm.

To formulate the complete culture medium, 100 mg/L dextran sulfate (average molecular weight=5,000 daltons) were added to the basal medium, and the complete medium was filtered through a low protein-binding filter and used immediately or stored at 4° C. under diminished light conditions until use.

Example 2

Formulation of Lower Protein and Protein-Free Culture Media

To produce a culture medium that was lower in protein, a basal medium was formulated as described in Example 1 except that transferrin was omitted from the formulation. In place of transferrin, either 40 μM $FeSO_4$-EDTA (Sigma; St. Louis, Mo.) or 60 μM $FeCl_3$-sodium citrate (Sigma) were added to the basal media, and this lower protein medium was then filtered and stored as described in Example 1.

To formulate a culture medium that is completely free of protein, a lower protein medium containing no transferrin is produced as described above, except that insulin is also omitted from the formulation and, instead, the final concentration of $ZnSO_4$ is increased to 0.354 mg/L as a substitute for insulin. Protein-free culture media are then filtered and stored as described in Example 1.

Example 3

Enrichment of Culture Medium

To provide a more enriched culture medium, the basal and/or complete media described above were supplemented with additional components. In one such enrichment, resulting in a culture medium that was low in animal protein (or animal protein-free), a formulation of hydrolyzed rice peptides (Hy-Pep Rice Extract; Quest International, Norwich, N.Y.) was added to the complete media of Example 1 or Example 2 (for animal protein-free media) at a concentration of about 100 mg/L (concentrations of about 1-1000 mg/L were found to be acceptable as well). Enriched culture media were then filter-sterilized and stored until use as described in Example 1. In an alternative formulation providing an enriched culture medium that is free of animal protein, a formulation of soy peptides (Hy-Soy; Quest International) is added at similar concentrations.

Other enriched culture media are prepared by adding one or more cytokines, such as growth factors at the following optimal concentrations: EGF (about 0.00001-10 mg/L), aFGF or bFGF (about 0.0001-10 mg/L), KGF (about 0.0001-10 mg/L) or HGF (about 0.00001-10 mg/L). Other cytokines are also optionally added at concentrations that are easily optimized by routine experimentation (e.g., dose-response curves). Cytokines are available commercially, for example, from Life Technologies, Inc. (Rockville, Md.).

Other enriched culture media are prepared by adding one or more animal peptides, such as bovine serum albumin (BSA), human serum albumin (HSA) or casein. Animal peptides are available commercially, for example from Sigma (St. Louis, Mo.), and are added to basal media or complete media at concentration ranges of about 1-30,000 mg/L; optimal concentrations for a particular application are easily determined by routine experimentation.

Other enriched culture media are prepared by adding one or more yeast peptides, such as yeast extract, yeastolate or yeast extract ultrafiltrate. Yeast extract and yeastolate are available commercially, for example from Difco (Norwell, Mass.), while yeast extract ultrafiltrate is prepared as described in U.S. Application No. 60/028,197, filed Oct. 10, 1996, the disclosure of which is incorporated herein by reference in its entirety. Yeast peptides are added to basal or complete media at concentration ranges of about 1-30,000 mg/L; optimal concentrations for a particular application are easily determined by routine experimentation.

Following preparation, enriched culture media are filter sterilized and stored as described in Example 1 for complete medium.

Example 4

Use of Culture Media for Suspension Culture of Epithelial Cells

To demonstrate the efficacy of the present media in suspension culture of anchorage-dependent cells, 293 human embryonic kidney cells transformed with adenovirus type 5 DNA were cultivated. Cultures of 293 cells in serum-supplemented media were weaned from serum by passage 2-3 times in OptiMEM medium (Life Technologies, Inc.; Rockville, Md.) supplemented with 2% normal horse serum in 165 $cm^2$ culture flasks. After the second or third passage, when cells reached 50-75% confluence, they were dislodged from the growth surfaces by gently rapping the flasks several times; trypsin or other proteolytic agents were not used, since such agents often cause irreversible damage to cells cultivated in low-serum or serum-free media. Cells were resuspended in the present culture media and triturated until aggregates dispersed into a single cell suspension, and cell concentration and viability was determined by trypan blue exclusion counting on a hemacytometer according to routine procedures.

Cells were then seeded into the present culture medium in Erlenmeyer flasks at a density of about $2.5-3.0\times10^5$ cells/ml. To minimize aggregation of the cells, the seed volume in the culture flasks was kept below about 20% of the total volume of the flask (e.g., for 125 ml flasks, total volume after dilution of cells was no more than about 21-22 ml; for 250 ml flasks, no more than about 40-45 ml). To maintain cells in suspension, flasks were then placed on a rotary shaker platform in an incubator (37° C., 8% $CO_2$/92% air) and shaken at 125 rpm. Cell densities and viabilities were determined at least every other day, and cells were subcultured when the density approached about $7.5-10.0\times10^5$ cells/ml by diluting cultures with fresh culture medium to a density of about $2.5-3.0\times10^5$ cells/ml. Subculturing was continued until aggregation of cells during cultivation appeared minimal.

Once cells were adapted to cultivation in suspension in the present culture media, the cultures were scaled up into larger-volume spinner flasks or bioreactors. Cells were concentrated from flask cultures by centrifugation at about 400 g for five minutes, pellets were resuspended by gentle trituration in the present media followed by vortex mixing for 45 seconds, and cells seeded into spinner flasks or bioreactors in the present media at a density of about $2.5-3.0\times10^5$ cells/ml. To minimize shearing of cells while maintaining the cells in suspension, for spinner cultures the spinner speed was set to about 150 rpm while for bioreactor cultures the impeller speed was set to about 70 rpm.

Figure 2:
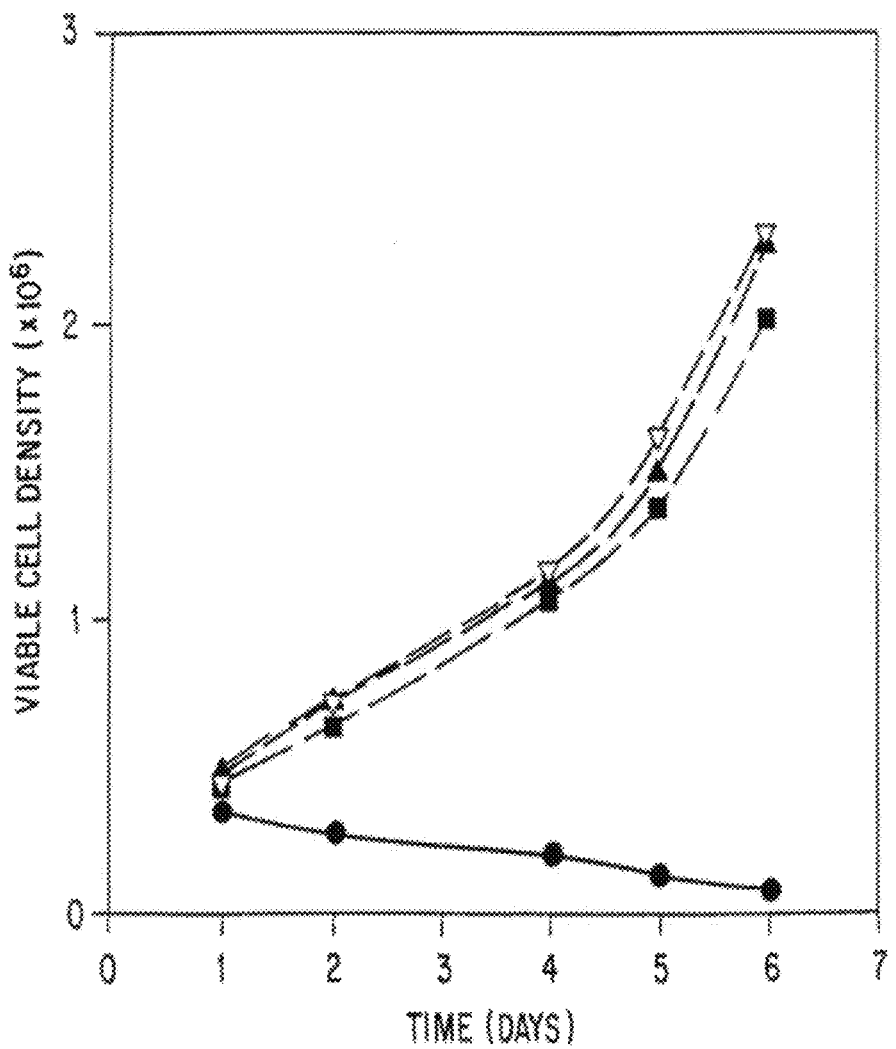
FIG. 2 depicts a line graph demonstrating viable cell density, over a seven day time course, of 293 cells cultured in suspension in the suspension culture media without transferrin (●), in the present culture media with human transferrin (■), or in the present culture media in which transferrin was replaced with 60 μM ferric chloride/sodium citrate chelate (▲) or with 40 μM ferrous sulfate/EDTA chelate ∇

In Erlenmeyer flask cultures of 293, cells, viable cell densities of about $2.5-3.0.\times10^6$ cells/ml were obtained (data not shown). As shown in FIG. 1, cell densities of up to $3.5-4\times10^6$ cells/ml, with nearly 100% viability, were obtained in bioreactors and spinner cultures of 293 cells in the complete media of the invention within 2-3 days after initiation of the cultures. Similar results were obtained with suspension cultures of HeLaS3 cervical epithelial cells (not shown). Lower-protein culture media of the invention, in which transferrin had been replaced by either $FeSO_4$-EDTA or $FeCl_3$-sodium citrate chelates, performed equivalently to complete media in supporting 293 cell growth (FIG. 2).

Together, these results demonstrate that the present culture media promote high-density suspension culture of anchorage-dependent epithelial cells and 293 cells in a serum-free, low-protein or protein-free environment.

Example 5

Production of Viruses by Suspension Cultures of 293 Cells

To examine the utility of the present media in virus production protocols, suspension cultures of 293 cells were prepared as described in Example 4 and infected with adenovirus. Infection of cells was performed directly in the suspension cultures by adding adenovirus at a MOI of about 5-50, and cultures were then maintained as in Example 4 for about 48-96 hours. Adenovirus was then harvested with the culture medium and titered on the permissive host cell line A549.

Figure 3:
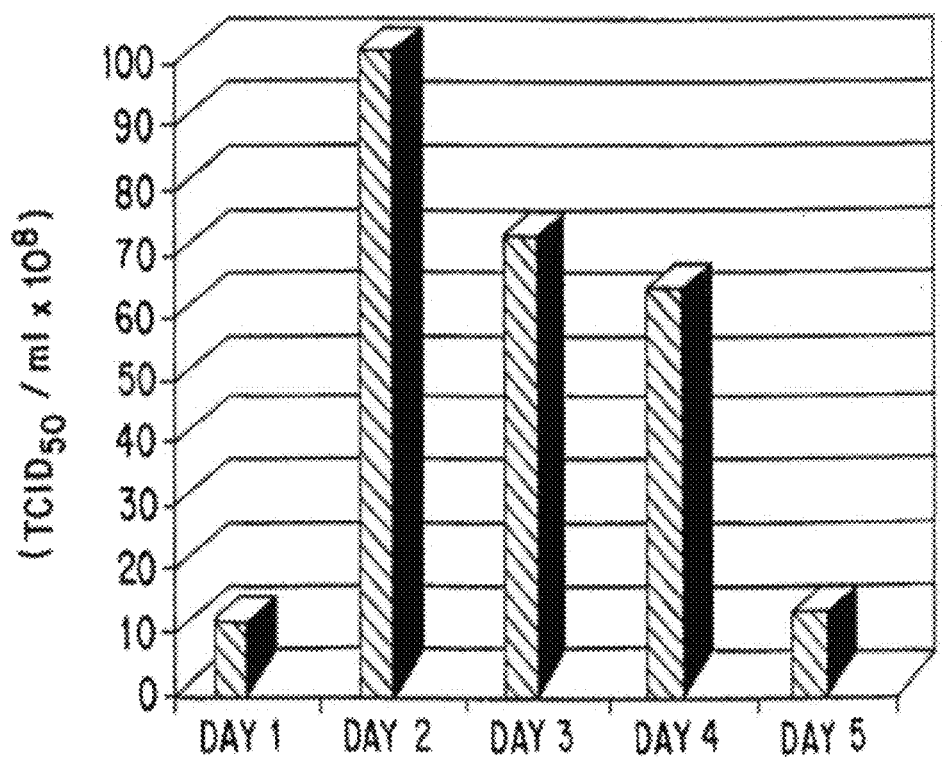
FIG. 3 depicts a bar graph demonstrating the production of adenovirus-5 in 293 cells cultured in the suspension culture media of the invention over a five-day time course. TCID50=tissue culture infectious dose-50%.

As shown in FIG. 3, adenovirus-infected 293 cells cultured in the media of the invention produced high titers of adenovirus-5 beginning at approximately day 2 post-infection and continuing through day 4. These results demonstrate that the present culture media facilitate the rapid, large-scale production of active viruses, such as adenovirus, in suspension cultures of 293 cells.

Example 6

Expression of Exogenous Genes by Suspension Cultures of 293 Cells

The utility of the present media in facilitating the production of recombinant polypeptides was also examined. Line 293 cells were plated in RPMI-1640 containing 10% FBS (growth medium) in six-well culture plates at $3 \times 10^5$ cells/ml, and one day later were transfected with 1.5 µg of pCMV.SPORT-β-galactosidase and 0.5 µg of pSV2neo plasmid DNAs (LTI; Rockville, Md.) in the presence of 12 µl of LipofectAMINE (LTI) using the standard LipofectAMINE protocol. At 24 hours post-transfection, cells in each well were subcultured into growth medium in a 10 cm² plate at final dilutions of 1:50, 1:200 and 1:500, and at 48 hours post-transfection the growth medium was replaced with selection medium (growth medium containing 500 µg/ml genetecin (LTI)). Medium was changed as necessary to remove nonviable cells, and resistant clones were selected with cloning cylinders and transferred to 24-well plates for adaptation to suspension culture.

Clones expressing β-galactosidase were adapted to suspension culture in the present culture media according to the procedures described in detail in Example 4. For all cultures, to maintain selective pressure on the cells, genetecin was included in the present culture media at concentrations of up to 50 µg/ml. Higher concentrations of genetecin are discouraged, since they may be toxic in serum-free, low-protein media such as those of the present invention.

Figure 4:
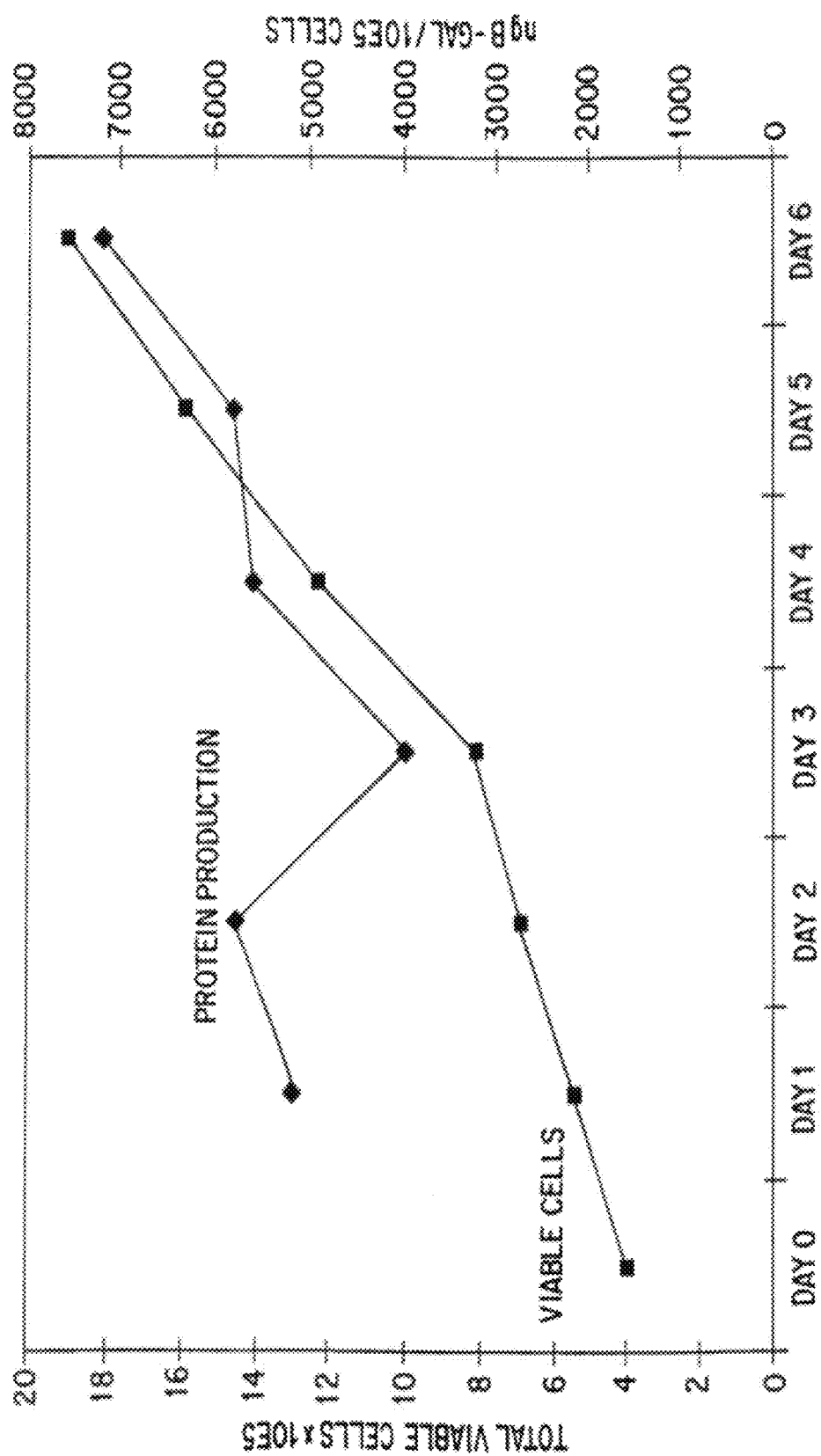
FIG. 4 depicts a line graph demonstrating β-galactosidase production, as a function of viable cell number over a six-day time course, by 293 cells cultured in the suspension culture media of the invention.

As shown in FIG. 4, significant quantities of β-galactosidase were produced by transfected 293 cells cultured in the present media, beginning at day 1 post-transfection and continuing throughout the six day course of the culture. These results demonstrate that the present culture media facilitate stable transfection of epithelial cells with exogenous genes, and the rapid, large-scale production of recombinant polypeptides by suspension cultures of 293 cells.

Figure 5A:
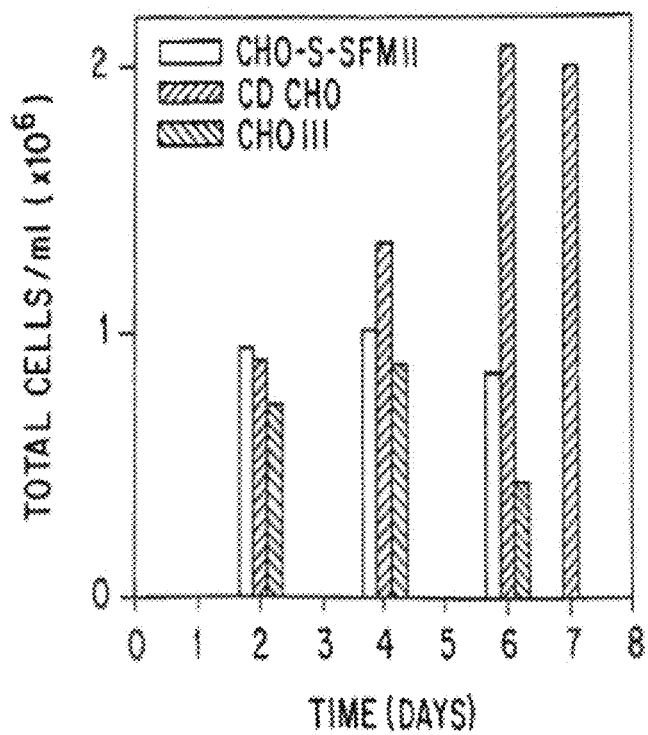
FIG. 5A depicts a bar graph showing the effect of low-protein/serum-free, essentially protein-free, and protein-free/chemically defined media on the growth of rβ-gal CHO cells.
Figure 5B:
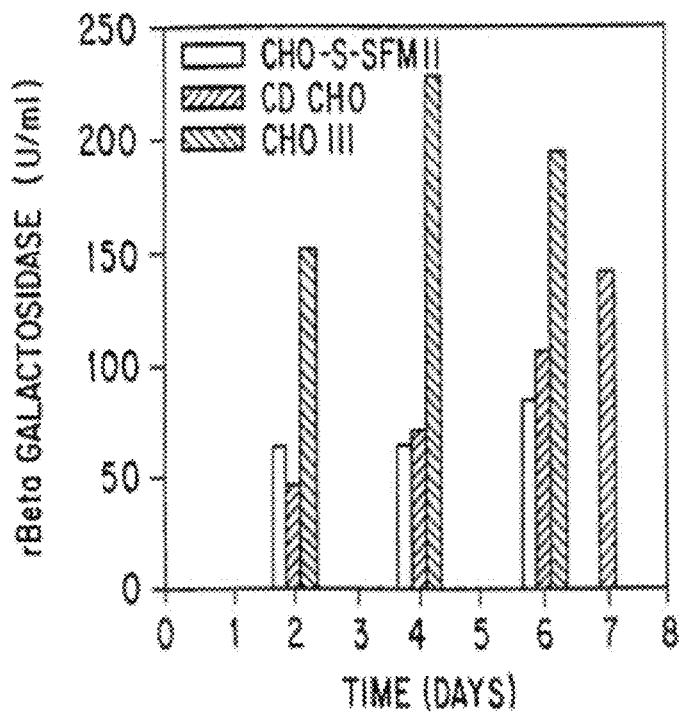
FIG. 5B depicts a bar graph showing the effect of low protein/serum-free, essentially protein-free, and protein-free/chemically defined media on the expression of rβ-galactosidase in rβgal CHO cells.

Example 7 rβ-gal CHO cells were planted at $3 \times 10^5$ cells/ml in CHO-S-SFM II medium (without hypoxanthine and thymidine), CD CHO medium, or CHO III Prototype medium. Samples were saved at various time points for determination of cell density and β-galactosidase expression levels. As shown in FIG. 5A, the highest cell density was obtained in CD CHO medium, which is the medium of the present invention. At day 4 of culturing, the highest level of β-galactosidase expression was observed in CHO III medium (FIG. 5B). By day 6 of culturing, whereas the level of β-galactosidase expression in cells grown in CHO III medium had declined, the level of β-galactosidase expression in cells grown in the replacement medium of the present invention (CD CHO medium) had increased. Indeed, the level of β-galactosidase expression in cells grown in CD CHO medium continued to increase at day 7 of culturing.

Figure 6A:
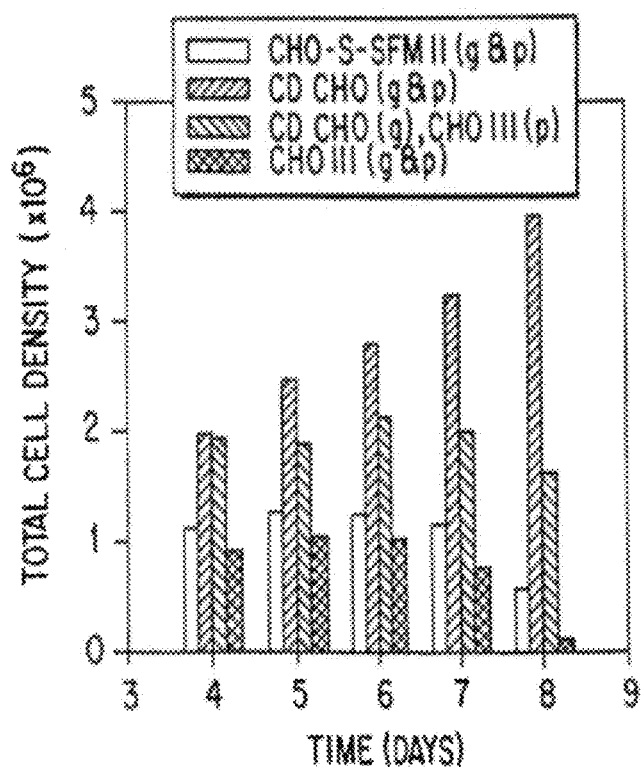
FIG. 6A depicts a bar graph showing the effect of low protein/serum-free, essentially protein-free, and protein free/chemically defined media on the growth of rβ-gal CHO cells. In this figure, "g" refers to the growth phase and "p" refers to the production phase.

Example 8 rβ-gal CHO cells were planted at $2 \times 10^5$ cells/mil in either CHO-S-SFM II medium (without hypoxanthine and thymidine), CD CHO medium, or CHO III medium. On day 3 post-planting, when the CD CHO cultures had reached approximately $1.2 \times 10^6$ cells/ml, the CD CHO cultures were centrifuged and resuspended in fresh CD CHO or CHO III media. By day 8, the CD CHO culture that had been changed to CHO III medium had reached a lower peak cell density than the culture kept in CD CHO medium (FIG. 6A).

Figure 6B:
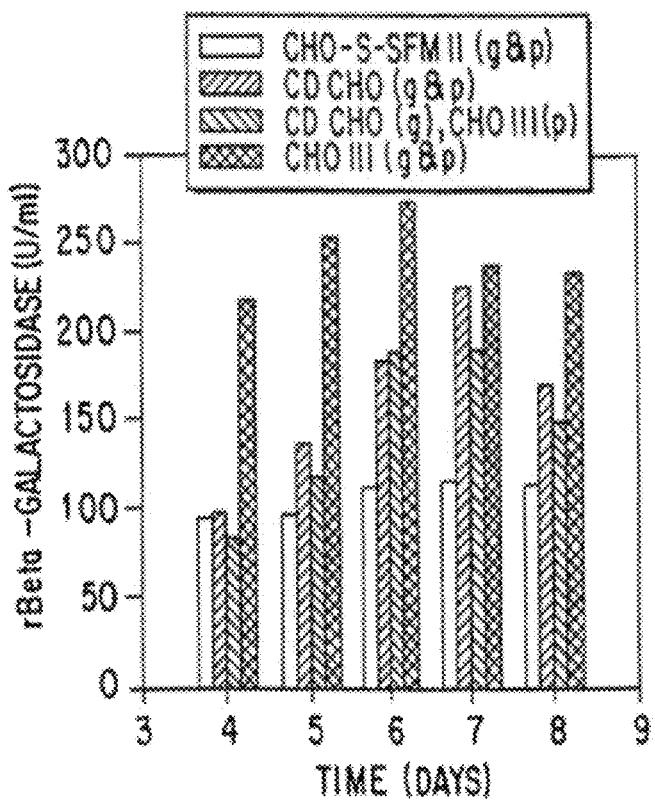
FIG. 6B depicts a bar graph showing the effect of low protein/serum-free, essentially protein-free, and protein-free/chemically defined media on the expression of rβ-galactosidase in rβ-gal CHO cells. In this figure, "g" refers to the growth phase and "p" refers to the production phase.

At day 7 of culturing, the level of rβ-galactosidase expression in cells grown in the replacement medium of the present invention (CD CHO medium) was comparable to the level in cells that were switched to CHO III medium (FIG. 6B).

Figure 7A:
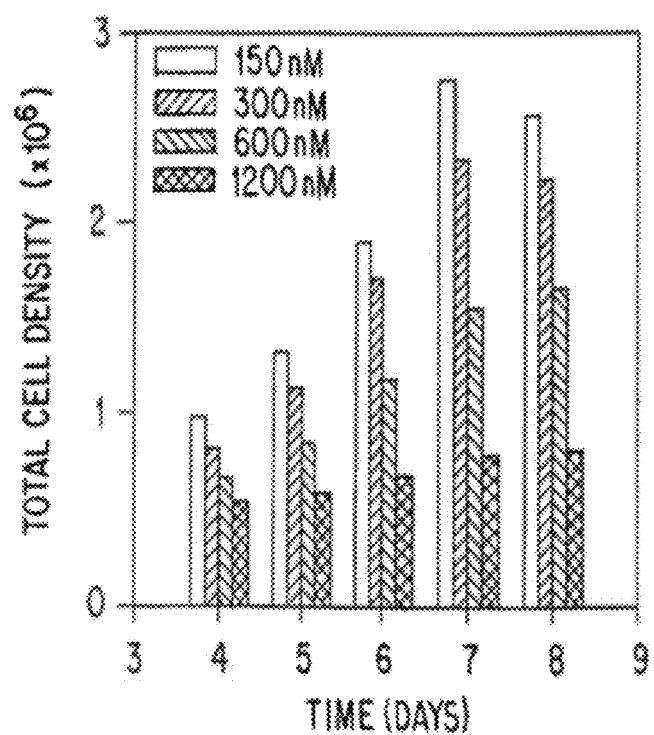
FIG. 7A depicts a bar graph showing the effect of methotrexate on the growth of rβ-gal CHO cells.
Figure 7B:
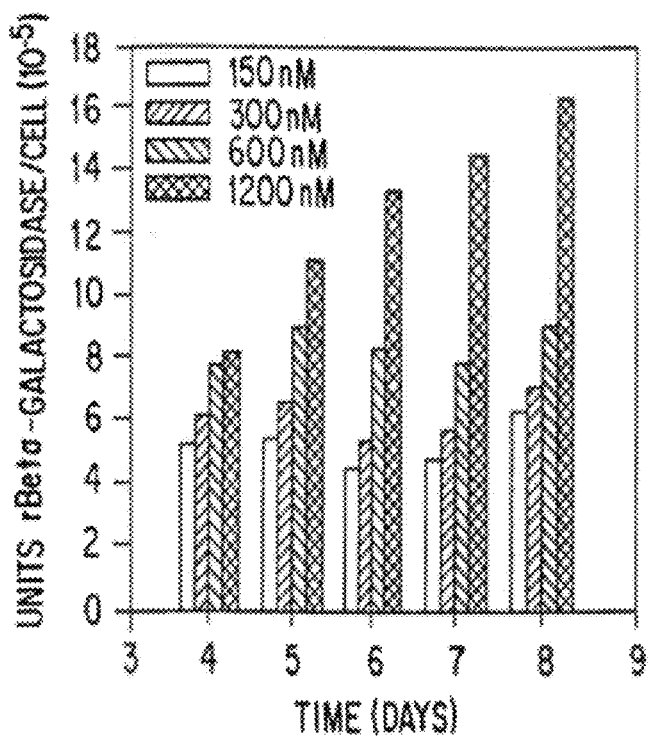
FIG. 7B depicts a bar graph showing the effect of methotrexate on the expression of rβ-galactosidase in rβ-gal CHO cells.

Example 9 rβ-gal CHO cells were planted at $1.8 \times 10^5$ cells/ml in CD CHO medium supplemented with increasing concentrations of methotrexate (MTX). Concentrations indicated are final concentrations. Samples were taken daily for determination of cell density and rβ-galactosidase expression. Although MTX concentration was inversely proportional to cell density (FIG. 7A), MTX concentration was proportional to rβ-galactosidase specific activity (FIG. 7B). Thus, the medium of the present invention, when supplemented with methotrexate, can be used to grow recombinant DHFR amplified CHO cells which express high levels of recombinant protein. Because the medium of the present invention is protein-free, the recombinant protein product can be easily purified.

Figure 8A:
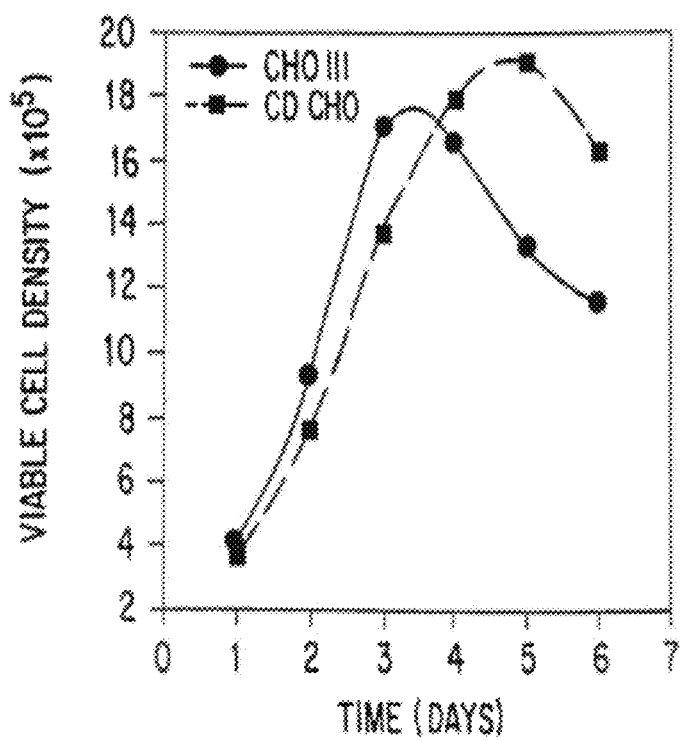
FIG. 8A depicts a graph showing the effect of essentially protein-free (●) and protein-free/chemically defined (■) media on rbGH CHO cells.
Figure 8B:
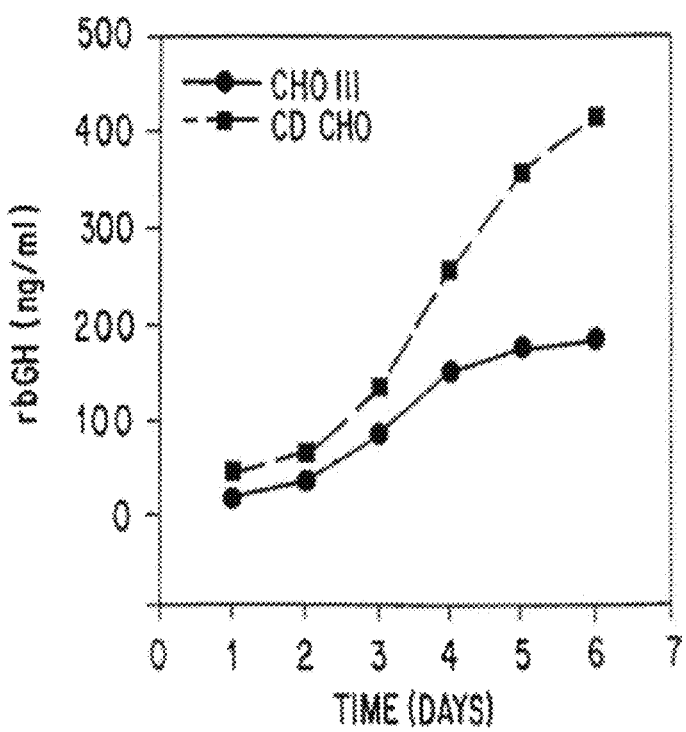
FIG. 8B depicts a graph showing the effect of essentially protein-free (●) and protein-free/chemically defined (●) media on rbGH expression in rbGH CHO cells.

Example 10 rbGH CHO cells were planted at $2 \times 10^5$/ml in 125 ml shake flasks (35 ml volume) in either CHO III medium or CD CHO medium. Daily samples were taken for determination of viable cell density and rbGH levels. The CD CHO cultures reached a higher peak cell density (FIG. 8A) and expressed higher levels of rbGH (FIG. 8B).

Figure 9A:
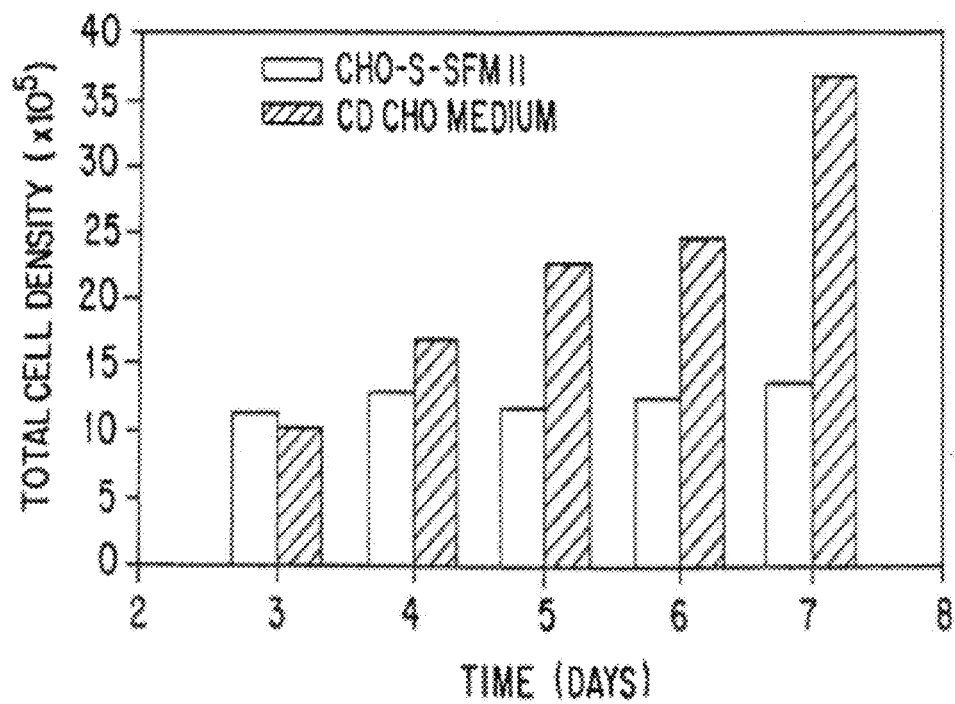
FIG. 9A depicts a bar graph showing the effect of low-protein, insulin- and transferrin-containing medium and a protein-free chemically defined medium on the growth of rβ-gal CHO cells.
Figure 9B:
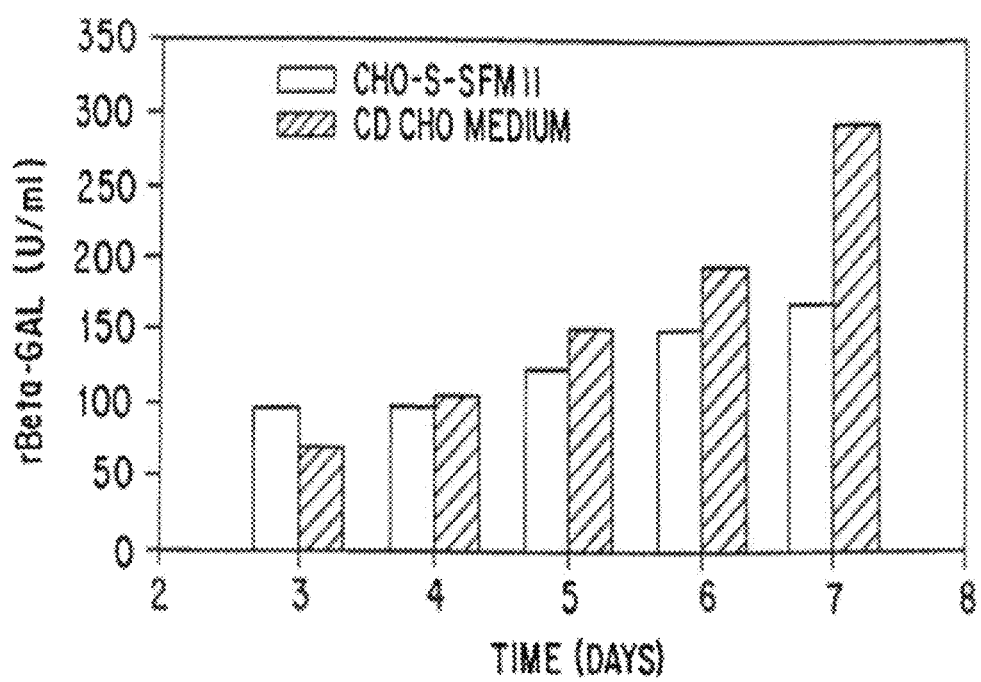
FIG. 9B depicts a bar graph showing the effect of low-protein, insulin- and transferrin-containing medium and a protein-free/chemically defined medium on rβ-galactosidase expression in rβ-gal CHO cells.

Example 11 rβ-gal CHO cells were planted at $3 \times 10^5$/ml in 125 ml shake flasks (20-35 ml volume) in either CHO-S-SFM II medium or CD CHO medium. Daily samples were taken for determination of viable cell density and rβ-gal levels. Total cell density continued to rise in CD CHO cultures (days 3 through 8, FIG. 9A), while total cell density remained constant in CHO-S-SFM II culture. rβ-gal levels continued to rise in both culture conditions, but CD CHO cultures expressed more total rβ-gal product (FIG. 9B). Thus, compared to a medium that contains insulin and transferrin, the medium of the present invention supports increased cell growth and level of protein expression.

Example 12 rβ-gal CHO cells were planted at $3 \times 10^5$/ml in 125 ml shake flasks (20-35 ml volume) in CD CHO, CHO III PFM, or FMX-8 media. FMX-8 medium is disclosed in Zang, M. et al., *Bio/Technology* 13:389-392 (1995).

Figure 10:
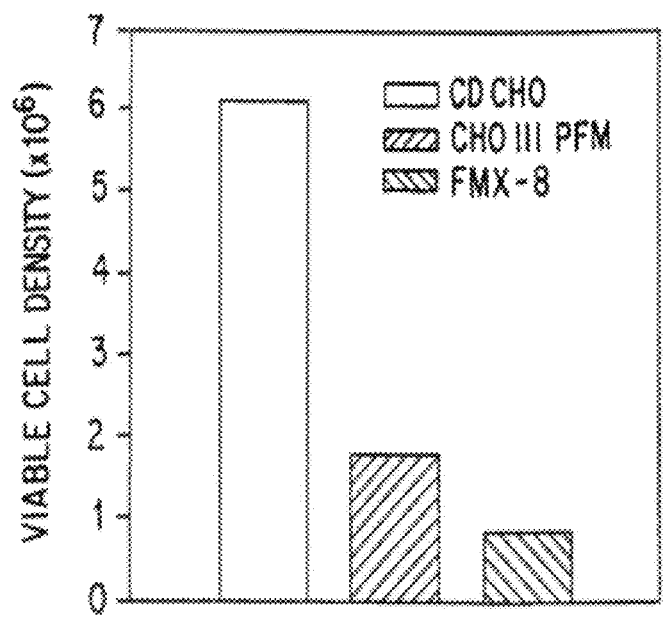
FIG. 10 depicts a bar graph showing the effect of CD CHO, CHO III, and FMX-8 media on the growth of rβ-gal CHO cells.

As shown in FIG. 10, after seven days of culturing, cells grown in CHO III PFM medium grew to a density about two-fold that of cells grown in FMX-8 medium. As shown in FIG. 10, cells grown in CD CHO medium grew to a density about three-fold that of cells grown in CD CHO medium and about six-fold that of cells grown in FMX-8 medium.

Figure 11:
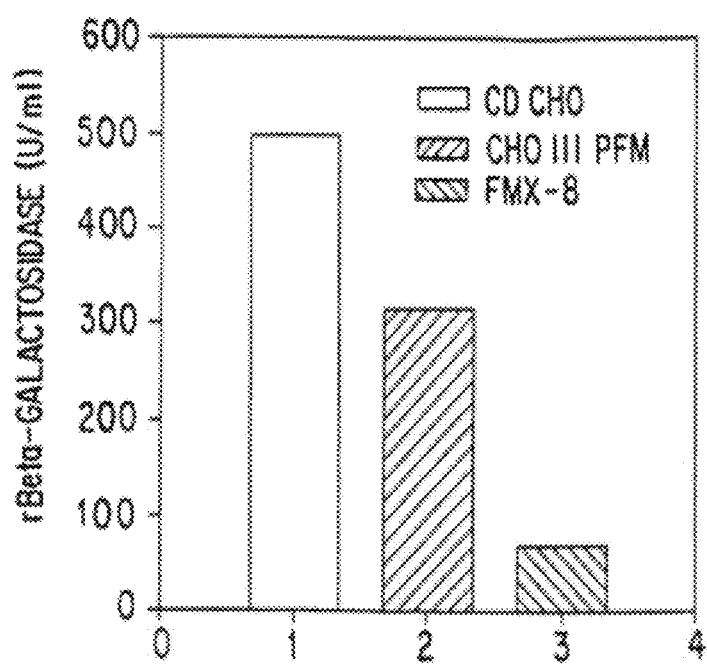
FIG. 11 depicts a bar graph showing the effect of CD CHO, CHO III, and FMX-8 media on rβ-gal expression in rβ-gal CHO cells.

As shown in FIG. 11, cells grown in CHO III PFM medium expressed rβ-gal at a level about three-fold that of cells grown in FMX-8 medium. As shown in FIG. 11, cells grown in CD CHO medium expressed rβ-gal at a level about 1.6-fold that of cells grown in CD CHO medium and about five-fold that of cells grown in FMX-8 medium. Thus, compared to the FMX-8 medium, the medium of the present invention supports increased levels of cell growth and protein expression.

Example 13

The CD CHO medium supports scaled-up cultures of mammalian cells as well. rβ-gal CHO cells were planted at $1-3\times10^5$/ml in 250 ml shake flasks (75 ml working volume) in CD CHO medium and cultured at pH 7.40, 50% air saturation, 37° C., while shaking at 125-135 r.p.m. For bioreactor experiments, rβ-gal cells were planted at $1-3\times10^5$/ml in a 5 L stirred tank Celligen bioreactor (3.8 L working volume) in CD CHO medium and cultured at pH 7.40, 50% air saturation, 37° C., while stirring at 90 r.p.m. The arrow indicates supplementation with 3 g/L glucose (final concentration) and 1 g/L glutamine (final concentration) at day nine of culturing.

Figure 12A:
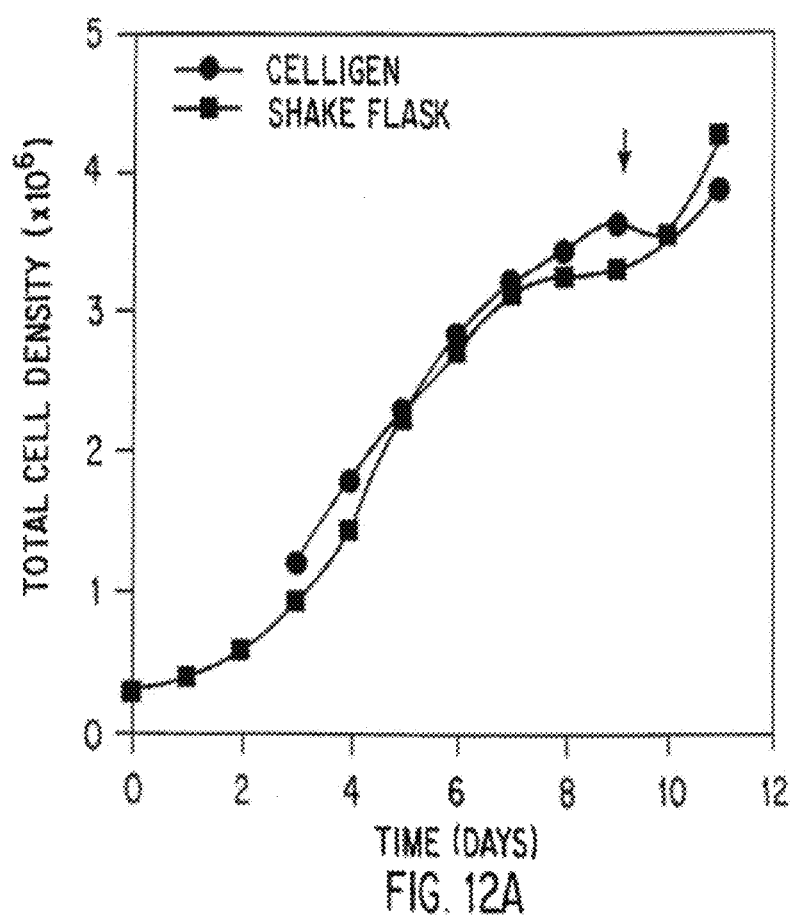
FIG. 12A shows the level of growth of rβ-gal CHO cells cultured in CD CHO medium in a shake flask (■) and in a bioreactor (●).
Figure 12B:
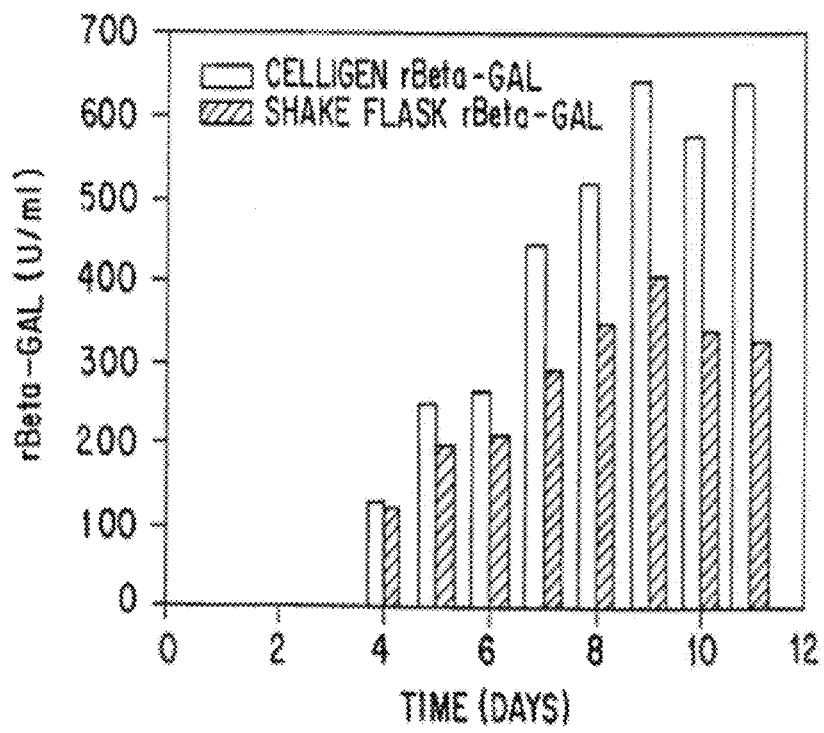
FIG. 12B shows the level of rβ-gal expression in cells cultured in CD CHO medium in a shake flask and in a bioreactor.

As shown in FIG. 12A, the growth kinetics of RCHO cells cultured in the bioreactor were similar to those observed in the shake flask. As shown in FIG. 12B, the level of rβ-gal expression was higher in cells cultured in the bioreactor. Supplementation with glucose and glutamine did not boost cell growth over the level reached on day nine. These results indicate that the CD CHO medium can be used successfully in scaled up cell culture.

Example 14

Figure 13:
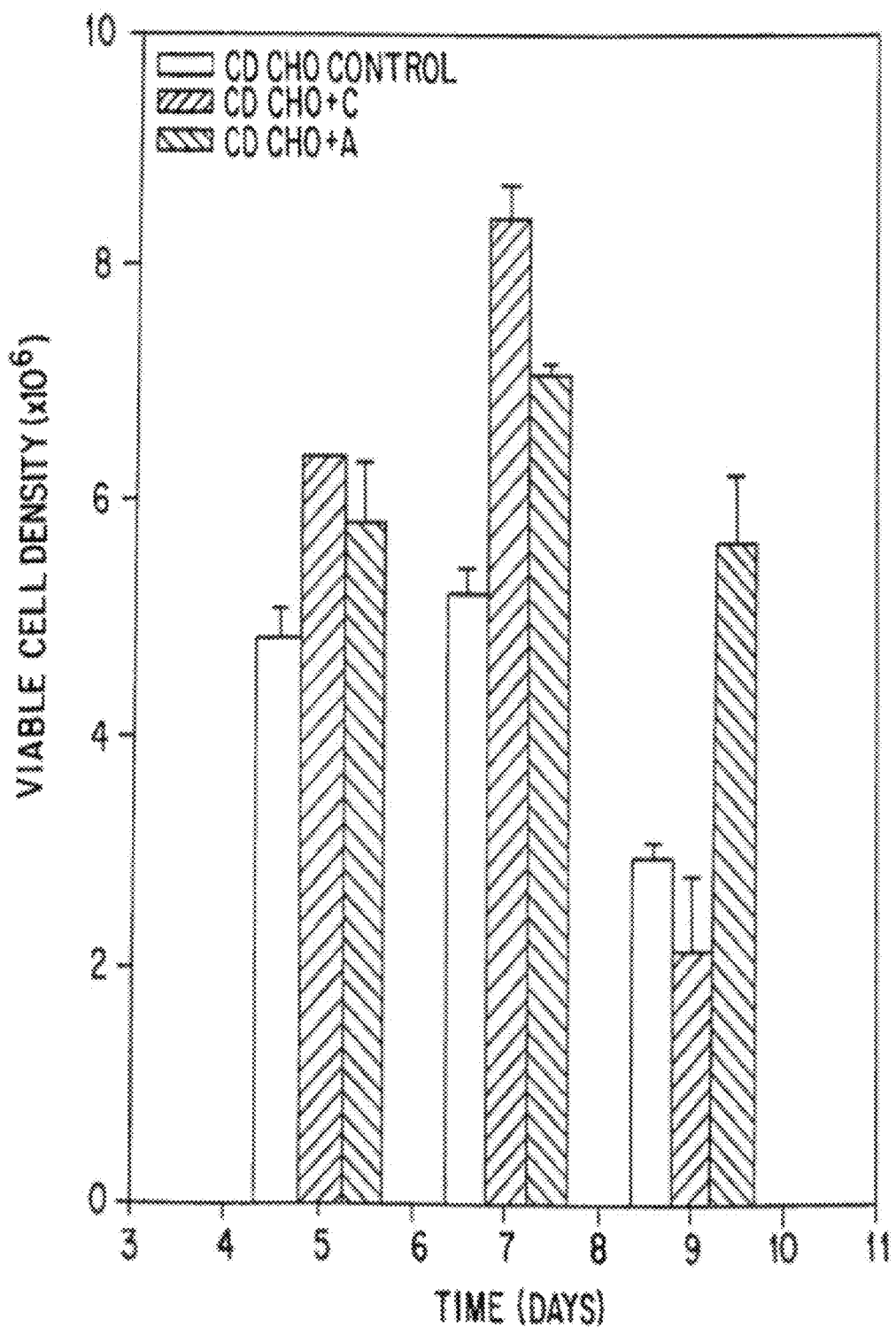
FIG. 13 depicts a bar graph showing the effect of dextran sulfate on the growth of rβ-gal CHO cells. In the figure, "A" is dextran sulfate (m.w. 5,000) and "C" is dextran sulfate (m.w. 500,000).
Figure 14:
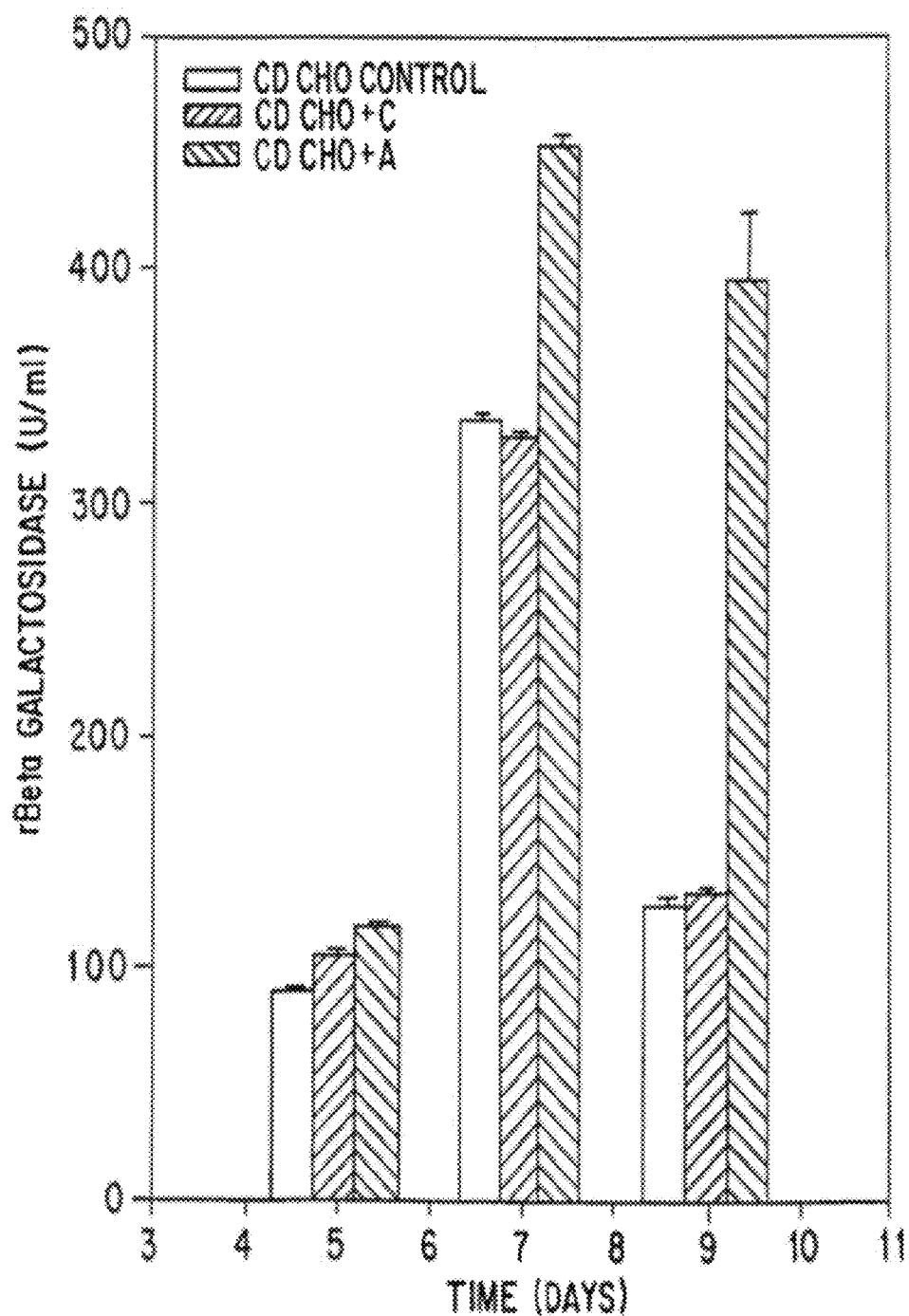
FIG. 14 depicts a bar graph showing the effect of dextran sulfate on rβ-gal expression in rβ.-gal CHO cells. In the figure, "A" is dextran sulfate (m.w. 5,000) and "C" is dextran sulfate (m.w. 500,000).

To determine the effect of the anticlumping agent dextran sulfate on cell growth and protein expression, recombinant cells were cultured in the presence or absence of dextran sulfate (molecular weight of either 5,000 or 500,000). rβ-gal CHO cells were planted at $3\times10^5$/ml in 125 ml shake flasks (20-35 ml volume) in CD CHO medium. Dextran sulfate was added to the medium, at the time of cell planting, to a final concentration of 25 μg/mL. Results are shown in FIGS. 13 and 14. In FIGS. 13 and 14, "A" is dextran sulfate (m.w. 5,000) and "C" is dextran sulfate (m.w. 500,000). CD CHO Control cells are cells to which dextran sulfate was not added. As shown in FIG. 13, cells grown medium containing dextran sulfate (m.w. 5,000) displayed increased cell growth and viability at days 5, 7, and 9. As shown in FIG. 13, cells grown in dextran sulfate (m.w. 500,000) displayed increased cell growth and viability at days 5 and 7, but not at day 9. As shown in FIG. 14, cells grown in dextran sulfate (m.w. 5,000) displayed an increase in the level of r.beta.-gal expression at days 5, 7, and 9. As shown in FIG. 14, cells grown in medium supplemented with dextran sulfate (m.w. 500,000) did not display enhanced expression.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing a recombinant protein in vitro, comprising culturing a recombinant CHO cell in suspension, in a serum-free and protein-free culture medium comprising zinc at a final concentration of about 0.00007 to 0.00073 g/L, and iron at a final concentration of about 0.00028 to 0.011 g/L, under conditions suitable for supporting the cultivation of the CHO cell to a density of about $5\times10^6$ cells/ml, in said suspension and expression of said recombinant protein, the conditions comprising culturing the CHO cell at about 37 degrees Celsius in a humidified atmosphere containing about 3-20% carbon dioxide in air, and wherein said serum-free and protein-free culture medium supports increased levels of cell growth as compared to culture in FMX-8 medium.

2. The method for producing a recombinant protein in vitro according to claim 1 wherein said recombinant protein is isolated.

3. The method for producing a recombinant protein in vitro according to claim 1 wherein the serum-free and protein-free culture medium comprises at least one polyanionic or polycationic compound.

4. The method for producing a recombinant protein in vitro according to claim 3 wherein said polyanionic compound is a polysulfonated or polysulfated compound.

5. The method for producing a recombinant protein in vitro according to claim 4 wherein said polysulfonated or polysulfated compound is selected from the group consisting of dextran sulfate, heparin, heparan sulfate, chondroitin sulfate, dermatan sulfate, pentosan sulfate and a sulfated proteoglycan.

6. The method for producing a recombinant protein in vitro according to claim 4 wherein said polysulfonated or polysulfated compound is dextran sulfate.

7. The method for producing a recombinant protein in vitro according to claim 6 wherein said dextran sulfate has an average molecular weight of about 5,000 to about 25,000 daltons.

8. The method for producing a recombinant protein in vitro according to claim 6 wherein said dextran sulfate has an average molecular weight of about 5,000 to about 10,000 daltons.

9. The method for producing a recombinant protein in vitro according to claim 1 wherein said recombinant CHO cell is cultured on a microcarrier.

10. The method for producing a recombinant protein in vitro according to claim 1 wherein said iron is a transferrin substitute and the zinc is an insulin substitute.

11. The method for producing a recombinant protein in vitro according to claim 1, wherein the serum-free and protein-free medium is sufficient for the growth of the recombinant CHO cell.

12. The method for producing a recombinant protein in vitro according to claim 1, wherein the expression of said recombinant protein is not required for the serum-free and protein-free cultivation of the cell.

13. The method for producing a recombinant protein in vitro according to claim 1, wherein the serum-free and protein-free growth of the cell does not require the co-production of an exogenous protein within the CHO cell.

* * * * *

UNITED STATES PATENT AND TRADEMARK OFFICE
CERTIFICATE OF CORRECTION

| | | |
|---|---|---|
| PATENT NO. | : 8,198,084 B2 | Page 1 of 1 |
| APPLICATION NO. | : 11/151647 | |
| DATED | : June 12, 2012 | |
| INVENTOR(S) | : Gorfien et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 281 days.

Signed and Sealed this

Fourth Day of November, 2014

Michelle K. Lee
*Deputy Director of the United States Patent and Trademark Office*